United States Patent
Ford et al.

(10) Patent No.: US 9,126,979 B2
(45) Date of Patent: Sep. 8, 2015

(54) COMPOUNDS FOR INHIBITING THE INTERACTION OF BCL2 WITH BINDING PARTNERS

(71) Applicant: Novartis AG, Basel (CH)

(72) Inventors: Daniel Ford, Windsor (GB); John Robert Porter, Oxfordshire (GB); Michael Scott Visser, Braintree, MA (US); Naeem Yusuff, Cambridge, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/366,857

(22) PCT Filed: Dec. 12, 2012

(86) PCT No.: PCT/US2012/069270
§ 371 (c)(1),
(2) Date: Jun. 19, 2014

(87) PCT Pub. No.: WO2013/096059
PCT Pub. Date: Jun. 27, 2013

(65) Prior Publication Data
US 2014/0343093 A1  Nov. 20, 2014

Related U.S. Application Data

(60) Provisional application No. 61/579,724, filed on Dec. 23, 2011.

(51) Int. Cl.
*C07D 401/10* (2006.01)
*A61K 31/4725* (2006.01)

(52) U.S. Cl.
CPC .................... *C07D 401/10* (2013.01)

(58) Field of Classification Search
None
See application file for complete search history.

(56) References Cited

U.S. PATENT DOCUMENTS

2010/0056517 A1  3/2010  Baell et al.

FOREIGN PATENT DOCUMENTS

| WO | 2006/023778 A2 | 3/2006 |
| WO | 2008/061208 A2 | 5/2008 |
| WO | 2011/029842 A1 | 3/2011 |
| WO | 2013/096049 A1 | 6/2013 |
| WO | 2013/096051 A1 | 6/2013 |
| WO | 2013/096055 A1 | 6/2013 |
| WO | 2013/096060 A1 | 6/2013 |

OTHER PUBLICATIONS

Neidle, Cancer Drug Design and Discovery. Elsevier/Academic Press. 2008:427-31.
Parikh et al., Phase II study of obatoclax mesylate (GX15-070), a small-molecule BCL-2 family antagonist, for patients with myelofibrosis. Clin Lymphoma Myeloma Leuk. Aug. 2010;10(4):285-9.
Porter et al., Tetrahydroisoquinoline amide substituted phenyl pyrazoles as selective Bcl-2 inhibitors. Bioorg Med Chem Lett. Jan. 1, 2009;19(1):230-3.

*Primary Examiner* — Zinna Northington Davis
(74) *Attorney, Agent, or Firm* — Brinks Gilson & Lione

(57) ABSTRACT

The present invention relates to compounds of formula I: in which $R^1$, $R^2$, $R^3$ and $R^4$ are as defined in the Summary of the Invention. Compounds of formula I are capable of disrupting the BCL-2 interations with proteins containing a BH3 domain. Disrupting this interaction can restore the anti-apoptotic function of BCL-2 in cancer cells and tumor tissue expressing BCL-2. The invention further provides a process for the preparation of compounds of the invention, pharmaceutical preparations comprising such compounds and methods of using such compounds in the treatment of cancerous diseases.

17 Claims, No Drawings

COMPOUNDS FOR INHIBITING THE INTERACTION OF BCL2 WITH BINDING PARTNERS

CROSS-REFERENCE TO RELATED APPLICATIONS

This application is a 371 of PCT/US2012/069270 filed Dec. 12, 2012, which claims the benefit of priority to U.S. provisional patent application No. 61/579,724, filed 23 Dec. 2011. The full disclosures of these applications are incorporated herein by reference in their entireties and for all purposes.

BACKGROUND

1. Field of the Invention

The present invention relates to compounds capable of disrupting the BCL-2 interactions with proteins containing a BH3 domain. Disrupting this interaction has the potential to restore the anti-apoptotic function of BCL-2 in cancer cells and tumor tissue expressing BCL-2. The invention further provides a process for the preparation of compounds of the invention, pharmaceutical preparations comprising such compounds and methods of using such compounds in the treatment of cancer.

2. Background of the Invention

Apoptosis, or programmed cell death, is important for normal embryological or anatomical development, host defense and suppression of oncogenesis. Faulty regulation of apoptosis has been implicated in cancers and many other human diseases which result from an imbalance between the process of cell division and cell death. BCL-2 belongs to a family of proteins which regulate apoptosis. BCL-2 contributes to cancer cell progression by preventing normal cell turnover caused by physiological cell-death mechanisms.

The expression levels of BCL-2 proteins correlates with resistance to a wide spectrum of chemotherapeutic drugs and γ-radiation therapy. Over-expression of BCL-2 has been observed in many forms of cancer. The following over-expression percentages in cancers have been observed: 20-40% in prostrate; 80-100% in hormone resistant prostrate; 60-80% in breast; 20-40% in non-small cell lung; 60-80% in small cell lung; 50-100% in colorectal; 65% in melanoma; 13% in head and neck; and 23% in pancreatic.

Biological approaches to modulating Bcl-2 function using anti-sense oligonucleotides or single-chain antibodies have been shown to enhance tumor cell chemosensitivity. Synergistic effects and complete tumor regression have been observed in vivo in the combined treatments with a combination of an anti-sense oligonucleotide (G3139) and docetaxel. Therefore, BCL-2 represents a highly attractive target for the development of a novel therapy for the treatment of many forms of cancers. In particular, the the need exists for small molecules that bind to BCL-2 and block its anti-apoptotic function in cancer and promote cell death in tumors. The present invention fulfills this need.

SUMMARY OF THE INVENTION

In one aspect, the present invention provides compounds of Formula I:

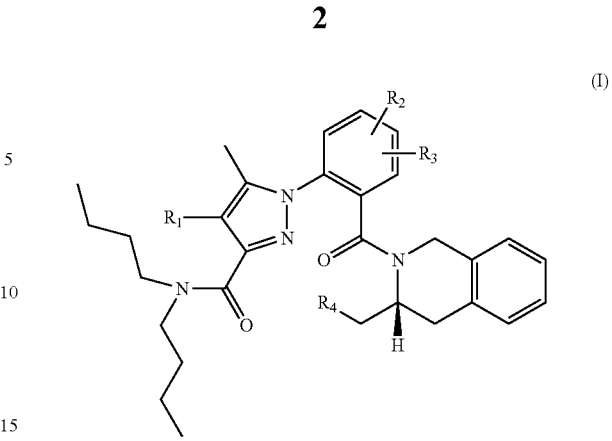

in which:

$R_1$ is selected from hydrogen and halo;

$R_2$ is selected from hydrogen and $C_{1-4}$alkyl; wherein $R_2$ is in the meta position and $R_3$ is in the para position relative to the pyrazole ring or $R_2$ is in the para position and $R_3$ is in the meta position relative to the pyrazole ring;

$R_3$ is selected from hydroxy and -L-$R_5$; wherein L is selected from —$OX_1C(O)$—, —$OX_1C(O)O$—, —$OX_1$— and —$OX_1C(O)NH$—; wherein $X_1$ is selected from a bond and branched or unbranched $C_{1-4}$alkylene; wherein said alkylene of $X_1$ can be unsubstituted or substituted with a group selected from carboxy-methyl, methoxy-carbonyl-methyl, methyl-carbonyl-amino and phenyl;

$R_4$ is selected from hydrogen, hydroxy, —$X_3NR_8R_9$, —$X_3C(O)OR_8$, —$X_3OR_8$, —$X_3C(O)NR_8R_9$ and —$X_3NR_8C(O)R_9$; wherein $X_3$ is selected from a bond and $C_{1-4}$alkylene; and $R_8$ and $R_9$ are independently selected from hydrogen, $C_{1-4}$alkyl and phenyl; or $R_8$ and $R_9$ together with the nitrogen to which $R_8$ and $R_9$ are attached form a 5 to 7 member saturated ring containing 1 to 3 groups or heteroatoms independently selected from C(O), $NR_{10}$, O and $S(O)_{0-2}$; wherein $R_{10}$ sis selected from hydrogen and $C_{1-4}$alkyl;

$R_5$ is selected from hydrogen, $C_{1-6}$alkyl, $C_{2-6}$alkenyl, cyclopropyl, imidazo[1,2-a]pyrimidinyl, 2-oxo-4-phenylpiperazin-1-yl, 4-(2-chlorobenzyl)-3-oxopiperazin-1-yl, imidazo[1,2-a]pyridinyl, benzo[d]isoxazolyl, naphtho[2,1-d][1,2,3]oxadiazol-5-yl, 1H-pyrrolo[2,3-b]pyridinyl, imidazo[2,1-b]thiazolyl, 1H-pyrazolo[3,4-b]pyridinyl, benzo[c][1,2,5]thiadiazolyl, 4-oxo-4,5,6,7-tetrahydrobenzofuranyl, 2-oxo-1,2,3,6-tetrahydropyrimidinyl, 1,2,4-oxadiazolyl, 2,3-dihydrobenzo[b][1,4]dioxin-2-yl, naphtho[2,3-d][1,3]dioxol-2-yl, 3,4-dihydro-2H-benzo[b][1,4]oxazin-7-yl, 2,3-dihydrobenzofuran-3-yl, chroman-8-yl, 3-oxo-3H-pyrazolyl, 6-oxo-1,6-dihydropyridazinyl, benzo[b]thiophenyl, benzo[b]furanyl, 2-oxo-1,2-dihydropyridinyl, 2-oxo-1,2,5,6,7,8-hexahydroquinolinyl, 4-oxo-1,4-dihydro-1,8-naphthyridinyl, 4-oxo-4H-pyrano[2,3-b]pyridinyl, 10,10-dioxido-9-oxo-9H-thioxanthen-3-yl, 5-oxopyrrolidin-3-yl, phenyl, quinolinyl, isoquinolinyl, phenoxy, phenylthio, benzoxy, phenyl-sulfonyl, furanyl, thiazolyl, oxazolyl, isoxazolyl, thienyl, pyrrolyl, quinolin-8-yloxy, pyrimidinyl, pyridinyl, pyrrolidinyl, pyrrolidinonyl, imidazolidine-2,4-dionyl, piperidinyl, piperazinyl, pyrazinyl, pyrazolyl, morpholino, oxomorpholino, indolyl, benzo[b]thiophenyl, benzo[b]furanyl, benzo[d][1,2,3]triazol and oxopiperazinyl; wherein said $C_{1-6}$alkyl, $C_{2-6}$alkenyl, cyclopropyl, imidazo[1,2-a]pyrimidinyl, benzo[d]isoxazolyl, imidazo[1,2-a]pyridinyl, 4-oxo-4,5,6,7-tetrahydrobenzofuranyl, 2-oxo-1,2,3,6-tetrahydropyrimidinyl, imidazo[2,1-b]thiazolyl, 1H-pyrrolo[2,3-b]pyridinyl, 1H-pyrazolo[3,4-b]pyridinyl, 1,2,4- oxadiazolyl, benzo[c][1,2,5]thiadiazolyl, 2,3-dihydrobenzo[b][1,4]dioxin-2-yl, naphtho[2,3-d][1,3]dioxol-2-yl, 3,4-dihydro-2H-benzo[b][1,4]oxazin-7-yl, 2,3-dihydrobenzofuran-3-yl, chroman-8-yl, 3-oxo-3H-pyrazolyl, 6-oxo-1,6-dihydropyridazinyl, 2-oxo-1,2-dihydropyridinyl, 2-oxo-1,2,5,6,7,8-hexahydroquinolinyl, 4-oxo-1,4-dihydro-1,8-naphthyridinyl, 4-oxo-4H-pyrano[2,3-b]pyridinyl, 10,10-dioxido-9-oxo-9H-thioxanthen-3-yl, 5-oxopyrrolidin-3-yl, phenyl, quinolinyl, isoquinolinyl, phenoxy, benzoxy, phenoxy-methyl, phenylthio, phenyl-sulfonyl, furanyl, thiazolyl, oxazolyl, isoxazolyl, thienyl, pyridinyl, pyrrolyl, quinolin-8-yloxy, pyrrolidinyl, pyrimidinyl, pyrrolidinonyl, piperazinyl, piperidinyl, pyrazinyl, pyrazolyl, morpholino, oxomorpholino, indolyl, benzo[d][1,2,3]triazol or oxopiperazinyl of $R_5$ is unsubstituted or substituted with 1 to 3 groups independently selected from halo, cyano, nitro, —$NR_6R_7$, $C_{1-4}$ alkyl, halo-substituted-$C_{1-4}$ alkyl, $C_{1-4}$ alkoxy, halo-substituted-$C_{1-4}$ alkoxy, halo-substituted-$C_{1-4}$ alkylthio, —$C(O)OR_6$, —$X_3OR_6$, —$C(O)R_6$, —$C(O)NR_6R_7$, —$NR_6S(O)_2X_3R_7$, —$X_3NR_6C(O)R_7$, —$S(O)_0R_6$, —$S(O)_{0-2}NR_6R_7$, phenyl, benzyl, piperidinyl, pyrrolidinyl, morpholino, morpholino-methyl, 1,2,4-oxadiazolyl, pyrazolyl, phenoxy, indolyl, (1H-1,2,4-triazolyl)methyl and benzoxy; wherein $R_6$ and $R_7$ are independently selected from hydrogen, $C_{1-4}$alkyl, $C_{3-8}$cycloalkyl, pyridinyl, phenyl, benzyl and naphthyl; wherein said phenyl, pyridinyl, benzyl, morpholino, morpholino-methyl, 1,3-dioxoisoindolinyl, 1,2,4-oxadiazolyl, pyrazolyl, indolyl and benzoxy substituents of $R_5$ or said pyridinyl and phenyl of $R_6$ can be unsubstituted or further substituted with a group selected from halo, nitro, amino-sulfonyl, $C_{1-4}$alkyl, $C_{1-4}$alkoxy and halo-substituted-$C_{1-4}$alkyl; wherein $X_3$ is selected from a bond and $C_{1-4}$alkylene; or the pharmaceutically acceptable salt thereof; with the proviso that compounds of formula I do not include the two compounds where $R_1$ is hydrogen, $R_2$ is hydrogen and $R_3$ is a group selected from —$OCH_2C(O)$-phenyl and —$OCH_2C(O)OH$; and the N-oxide derivatives, prodrug derivatives, protected derivatives, individual isomers and mixture of isomers thereof; and the pharmaceutically acceptable salts and solvates (e.g. hydrates) of such compounds.

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients.

In a third aspect, the present invention provides a method of treating a disease in an animal in which modulation of BCL-2 activity can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease in an animal in which BCL-2 activity contributes to the pathology and/or symptomology of the disease.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

Definitions

The general terms used hereinbefore and hereinafter preferably have within the context of this disclosure the following meanings, unless otherwise indicated, where more general terms wherever used may, independently of each other, be replaced by more specific definitions or remain, thus defining more detailed embodiments of the invention:

"Alkyl" as a group and as a structural element of other groups, for example halo-substituted-alkyl and alkoxy, can be either straight-chained or branched. $C_{1-4}$-alkoxy includes, methoxy, ethoxy, and the like. Halo-substituted alkyl includes difluoromethyl, trifluoromethyl, pentafluoroethyl, and the like.

"Aryl" means a monocyclic or fused bicyclic aromatic ring assembly containing six to ten ring carbon atoms. For example, aryl may be phenyl or naphthyl, preferably phenyl. "Arylene" means a divalent radical derived from an aryl group.

"Heteroaryl" is as defined for aryl above where one or more of the ring members is a heteroatom. For example $C_{5-10}$heteroaryl is a minimum of 5 members as indicated by the carbon atoms but that these carbon atoms can be replaced by a heteroatom. Consequently, $C_{5-10}$heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc.

"Heterocycloalkyl" means cycloalkyl, as defined in this application, provided that one or more of the ring carbons indicated, are replaced by a moiety selected from —O—, —N═, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, pyrrolidinyl-2-one, piperazinyl, piperidinyl, piperidinylone, 1,4-dioxa-8-aza-spiro[4.5]dec-8-yl, thiomorpholino, sulfanomorpholino, sulfonomorpholino, etc.

"Halogen" (or halo) preferably represents chloro or fluoro, but may also be bromo or iodo.

Compounds of the formula I may have different isomeric forms. For example, any asymmetric carbon atom may be present in the (R)-, (S)- or (R,S)-configuration, preferably in the (R)- or (S)-configuration. Substituents at a double bond or especially a ring may be present in cis- (═Z-) or trans (═E-) form. The compounds may thus be present as mixtures of isomers or preferably as pure isomers, preferably as pure diastereomers or pure enantiomers.

Where the plural form (e.g. compounds, salts) is used, this includes the singular (e.g. a single compound, a single salt). "A compound" does not exclude that (e.g. in a pharmaceutical formulation) more than one compound of the formula I (or a salt thereof) is present, the "a" merely representing the indefinite article. "A" can thus preferably be read as "one or more", less preferably alternatively as "one".

Wherever a compound or compounds of the formula I are mentioned, this is further also intended to include N-oxides of such compounds and/or tautomers thereof.

The term "and/or an N-oxide thereof, a tautomer thereof and/or a (preferably pharmaceutically acceptable) salt thereof" especially means that a compound of the formula I may be present as such or in mixture with its N-oxide, as tautomer (e.g. due to keto-enol, lactam-lactim, amide-imidic acid or enamine-imine tautomerism) or in (e.g. equivalency reaction caused) mixture with its tautomer, or as a salt of the compound of the formula I and/or any of these forms or mixtures of two or more of such forms.

The present invention also includes all suitable isotopic variations of the compounds of the invention, or pharmaceutically acceptable salts thereof. An isotopic variation of a compound of the invention or a pharmaceutically acceptable salt thereof is defined as one in which at least one atom is replaced by an atom having the same atomic number but an atomic mass different from the atomic mass usually found in nature. Examples of isotopes that may be incorporated into the compounds of the invention and pharmaceutically acceptable salts thereof include, but are not limited to, isotopes of hydrogen, carbon, nitrogen and oxygen such as as $^2H$, $^3H$, $^{11}C$, $^{13}C$, $^{14}C$, $^{15}N$, $^{17}O$, $^{18}O$, $^{35}S$, $^{18}O$, $^{35}S$, $^{18}F$, $^{36}Cl$ and $^{123}I$. Certain isotopic variations of the compounds of the invention and pharmaceutically acceptable salts thereof, for example, those in which a radioactive isotope such as $^3H$ or $^{14}C$ is incorporated, are useful in drug and/or substrate tissue distribution studies. In particular examples, $^3H$ and $^{14}C$ isotopes may be used for their ease of preparation and detectability. In other examples, substitution with isotopes such as $^2H$ may afford certain therapeutic advantages resulting from greater metabolic stability, such as increased in vivo half-life or reduced dosage requirements. Isotopic variations of the compounds of the invention or pharmaceutically acceptable salts thereof can generally be prepared by conventional procedures using appropriate isotopic variations of suitable reagents.

DESCRIPTION OF PREFERRED EMBODIMENTS

The present invention relates to the discovery of compounds of Formula I capable of inhibiting the interaction between BCL-2 and BH3. In one embodiment, with respect to compounds of Formula I, are compounds of Formula Ia:

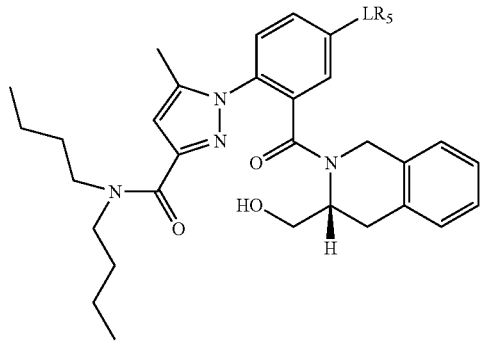

(Ia)

in which: L is selected from —OCH$_2$C(O)—, —OCH$_2$C(O)O—, —O— and —OCH$_2$C(O)NH—; and R$_5$ is selected from hydrogen, methyl, ethyl, phenyl and benzyl; wherein said phenyl or benzyl are unsubstituted or substituted with halo.

In a further embodiment are compounds selected from:

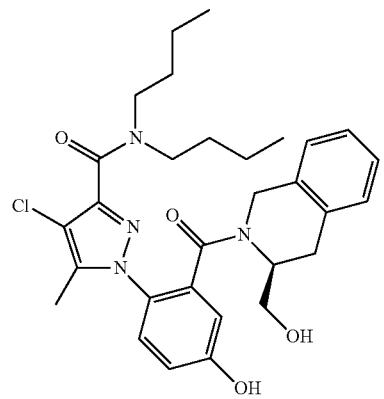

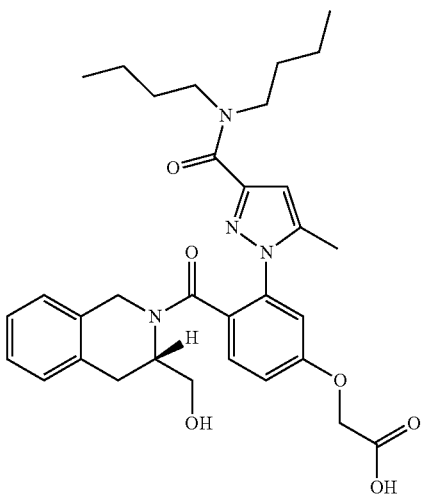

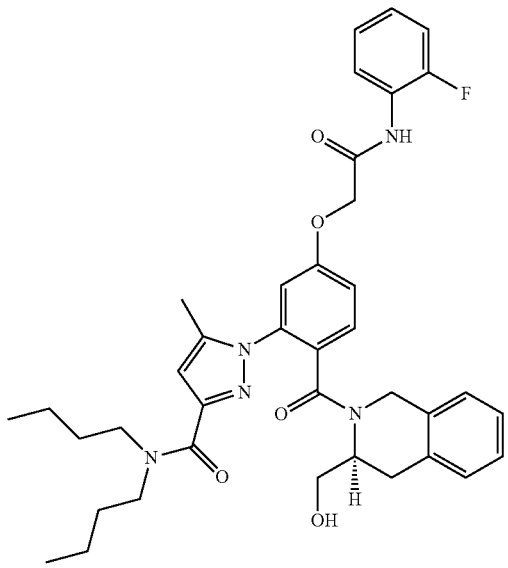

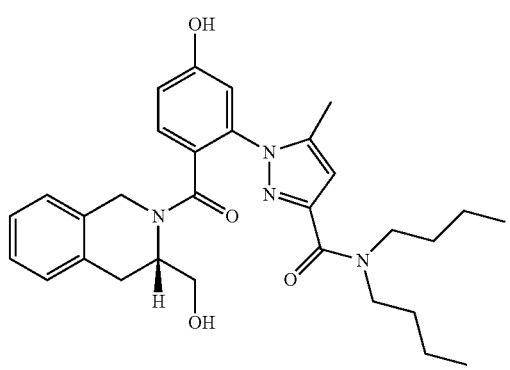
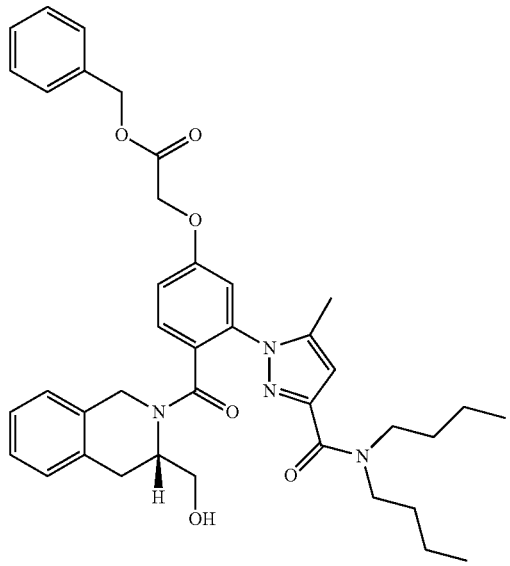
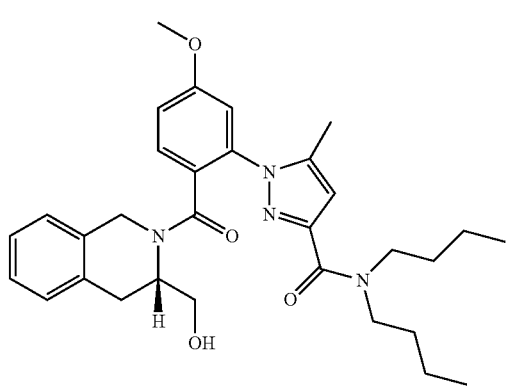
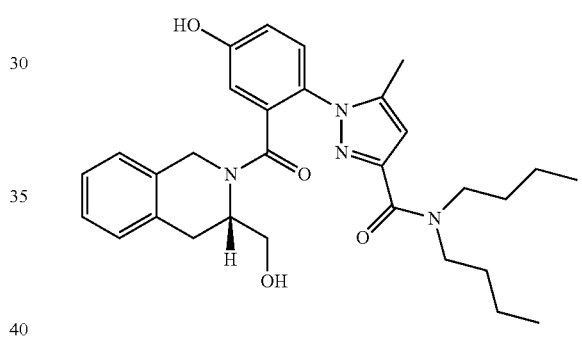
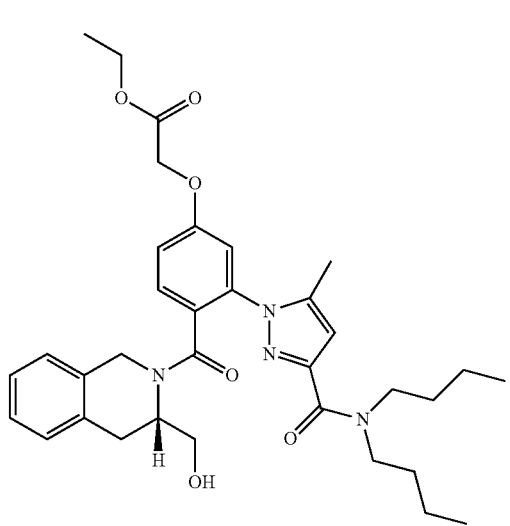
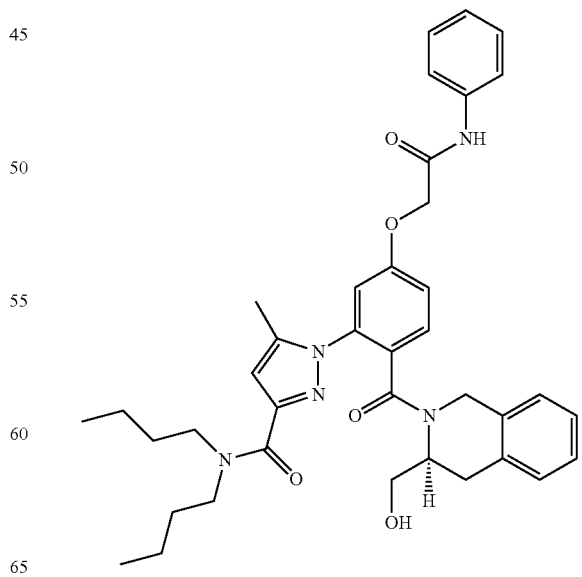

-continued

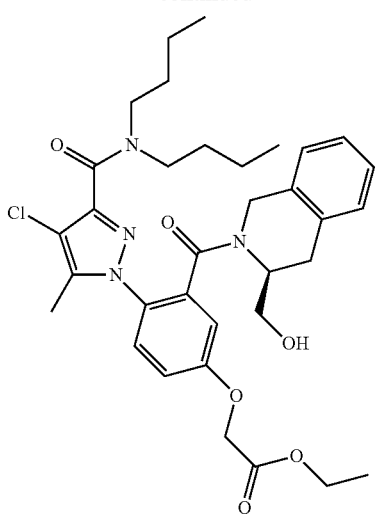

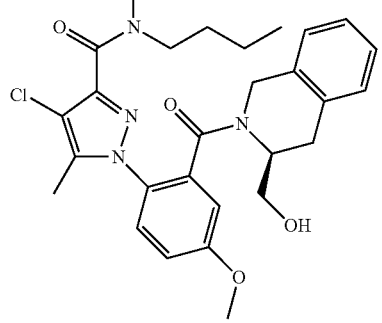

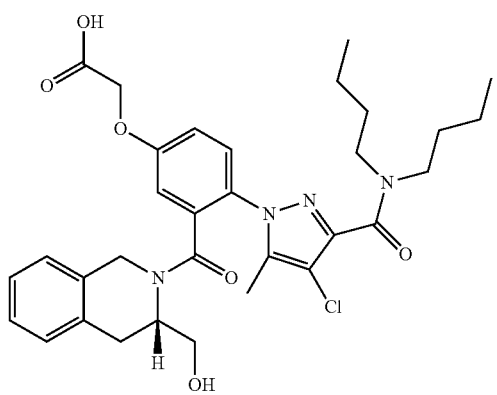

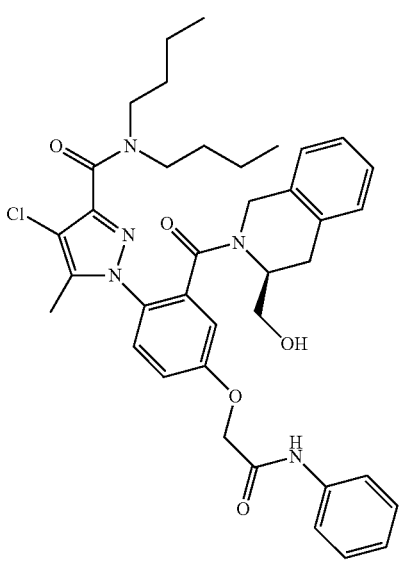

Pharmacology and Utility

The present invention makes available methods and compounds capable of inhibiting the interaction between BCL-2 and proteins containing a BH3 domain. One aspect of the present invention relates to a method of treating a BCL-2-mediated disorder, comprising the step of administering to a patient in need thereof a therapeutically effective amount of a compound of formula I as defined in the Summary of the Invention.

BCL-2 inhibitors have been shown to be active against a number of cancer cell lines as a single agent, including, but not limited to, breast cancer (US 2003/0119894, published PCT applications WO 02/097053 and WO 02/13833), lymphomas (*Nature* (2005) 435, 677-681), small cell lung cancer (*Nature* (2005) 435, 677-681), head and neck cancer (published PCT application WO 02/097053), and leukemias (published PCT application WO 02/13833).

BCL-2 was originally identified at the chromosomal breakpoint of t(14;18)-bearing B-cell lymphomas and belongs to a growing family of proteins which regulate apoptosis. (Gross, A; McDonnell, J M; Korsmeyer, S. J. BCL-2 family members and the mitochondria in apoptosis. Genes & Development 1999, 13, 1899-1911, Cory, S.; Huang, D. C. S.; Adams, J. M. The BCL-2 family: roles in cell survival and oncogenesis. Oncogene, 2003 22, 8590-8607. Danial, N. N.; Korsmeyer, S. J. Cell death: Critical control points. Cell 2004, 116, 205-218. Chao, D. T.; Korsmeyer, S. J. BCL-2 family: regulators of cell death. Annu. Rev. Immunol. 1998, 16, 395-419). Apoptosis, Christopher Potten, James Wilson, Cambridge University Press, 2004). The BCL-2 family of proteins include both anti-apoptotic molecules, such as BCL-2 and BCL-XL, and pro-apoptotic molecules, such as BAX, BAK, BID and BAD. BCL-2 contributes to cancer cell progression by preventing normal cell turnover caused by physiological cell-death mechanisms. Over-expression of BCL-2 has been observed in 70% of breast cancer and many other forms of cancer (Buolaniwini, J. K. Novel anticancer drug discovery. Curr. Opin. Chem. Biol. 1999, 3, 500-509). The expression levels of BCL-2 proteins also correlate with resistance to a wide spectrum of chemotherapeutic drugs and γ-radiation therapy (Reed, J. C.; Miyashita, T.; Takayama, S.; Wang, H.-G.; Sato, T.; Krajewski, S.; Aime-Sempe, C.; Bodrug, S.; Kitada, S.; Hanada, M. BCL-2 family proteins: Regulators of cell-death involved in the pathogenesis of cancer and resistance to therapy. J. Cell. Biochem. 1996, 60, 23-32; Reed, J. C. BCL-2 family proteins: strategies for overcoming chemoresistance in cancer. Advances in Pharmocology 1997, 41, 501-553; Strasser, A.; Huang, D. C. S.; Vaux, D. L. The role of the BCL-2/ced-9 gene family in cancer and general implications of defects in cell death control for tumorigenesis and resistance to chemotherapy. Biochem. Biophys. Acta 1997, 1333, F151-F189; DiPaola, R. S.; Aisner, J. Overcoming BCL-2- and p53-mediated resistance in prostate cancer. Semin. Oncol. 1999, 26, 112-116).

Members of the BCL-2 family of proteins represent key regulators of apoptosis, with pro-apoptotic (e.g., BAX, BAK, BID, BIM, NOXA, PUMA) and anti-apoptotic function (e.g., BCL-2, BCL-XL, MCL-1). Selective and competitive dimerization between pro- and anti-apoptotic members of the family determines the fate of a cell given pro-apoptotic stimulus. Although the precise roles of BCL-2 and BCL-XL in cancer are not completely understood, there are several lines of evidence that suggest that BCL-2 and BCL-XL not only contribute to cancer progression by preventing normal cell turnover, but also play a role in the resistance of cancer cells to current cancer treatments. Experimental over-expression of BCL-2 (BCL-XL) renders cancer cells resistant to a wide spectrum of chemotherapeutic agents and radiation (BCL-2 family proteins: Regulators of cell-death involved in the pathogenesis of cancer and resistance to therapy. J. Cell. Biochem. 1996, 60, 23-32; Reed, J. C). BCL-2 and/or BCL-XL are over-expressed in more than 50% of all tumors as shown below (from Wang, S.; Yang, D.; Lippman, M. E. Targeting BCL-2 and BCL-XL with nonpeptidic small-molecule antagonists. Seminars in Oncology, 2003, 5, 133-142).

| Cancer | BCL-2 over-expression (%) | BCL-XL over-expression (%) |
|---|---|---|
| Prostate | 20-40 | 100 |
| hormone resistant | 80-100 | — |
| Breast | 60-80 | 40-60 |
| Non-small cell lung | 20-40 | — |
| Small cell lung | 60-80 | — |
| Colorectal | 50-100 | 83 |
| Melanoma | 65 | 90 |
| Multiple myeloma (at relapse) | — | 77 |
| Head and Neck | 13 | 52-75 |
| Pancreatic | 23 | 90 |
| Hepatocellular carcinoma | — | 80 |

Biological approaches to modulating BCL-2 function using anti-sense oligonucleotides or single-chain antibodies have been shown to enhance tumor cell chemosensitivity (Ziegler, A.; Luedke, G. H.; Fabbro, D.; Altmann, K. H.; Stahel, R. A.; Zangemeister-Wittke, U. Induction of apoptosis in small-cell lung cancer cells by an antisense oligodeoxynucleotide targeting the BCL-2 coding sequence. J. Natl. Cancer. Inst. 1997, 89, 1027-1036; Webb, A.; Cunningham, D.; Cotter, F.; Clarke, P. A.; Di Stefano, F.; Ross, P.; Corpo, M.; Dziewanowska, Z. BCL-2 antisense therapy in patients with non-hodgkin lymphoma. Lancet 1997, 349, 1137-1141; Cotter, F. E. Phase I clinical and pharmacokinetic study of BCL-2 antisense oligonucleotide therapy in patients with non-hodgkin's lymphoma. J. Clin. Oncol. 2000, 18, 1812-1823; Piche, A.; Grim, J.; Rancourt, C.; Gomez-Navarro, J.; Reed, J. C.; Curiel, D. T. Modulation of BCL-2 protein levels by an intracellular anti-BCL-2 single-chain antibody increases drug-induced cytotoxicity in the breast cancer cell line MCF-7. Cancer Res. 1998, 58, 2134-2140).

It has been shown that an anti-sense oligonucleotide (G3139) (Raynaud, F. I.; Orr, R. M.; Goddard, P. M.; Lacey, H. A.; Lancashire, H.; Judson, I. R.; Beck, T.; Bryan, B.; Cotter, F. E. Pharmacokinetics of G3139, a phosphorothioate oligodeoxynucleotide antisense to BCL-2, after intravenous administration or continuous subcutaneous infusion to mice. J. Pharmacol. Exp. Ther. 1997, 281, 420-427), designed to hybridize to sequence in BCL-2 mRNA, inhibits BCL-2 expression, induces apoptosis and inhibits cell growth in human breast cancer cells having Bcl-2 over-expression (Chen, H. X., Marchall, J. L., Trocky, N., Baidas, S., Rizvi, N., Ling, Y., Bhagava, P., Lippman, M. E., Yang, D., and Hayes, D. F. A Phase I study of BCL-2 antisense G3139 (Genta) and weekly docetaxel in patients with advanced breast cancer and other solid tumors. Proceedings of American Society of Clinical Oncology, 2000). Importantly, synergistic effects and complete tumor regression were observed in vivo in the combined treatments of G3139 with docetaxel. Therefore, BCL-2 represents a highly attractive target for the development of a novel therapy for the treatment of many forms of cancers.

In certain embodiments, the present invention relates to the aforementioned method, wherein said BCL-2-mediated disorder is cancer.

In certain embodiments, the present invention relates to the aforementioned method, wherein said cancer is selected from the group consisting of acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia, chronic lymphocytic leukemia, polycythemia Vera, Hodgkin's disease, non-Hodgkin's disease; multiple myeloma, Waldenstrom's macroglobulinemia, heavy chain disease, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, stadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, and endometrial cancer.

In certain embodiments, the present invention relates to the aforementioned method, wherein said cancer is follicular lymphoma, diffuse large B-cell lymphoma, mantle cell lymphoma, chronic lymphocytic leukemia prostate cancer, breast cancer, neuroblastoma, colorectal, endometrial, ovarian, lung cancer, hepatocellular carcinoma, multiple myeloma, head and neck or testicular cancer.

In certain embodiments, the present invention relates to the aforementioned method, wherein said cancer over-expresses BCL-2.

In certain embodiments, the present invention relates to the aforementioned method, wherein said cancer is dependent upon BCL-2 for growth and survival.

In certain embodiments, the present invention relates to the aforementioned method, wherein said compound is administered parenterally.

In certain embodiments, the present invention relates to the aforementioned method, wherein said compound is administered intramuscularly, intravenously, subcutaneously, orally, pulmonary, intrathecally, topically or intranasally.

In certain embodiments, the present invention relates to the aforementioned method, wherein said compound is administered systemically.

In certain embodiments, the present invention relates to the aforementioned method, wherein said patient is a mammal.

In certain embodiments, the present invention relates to the aforementioned method, wherein said patient is a primate.

In certain embodiments, the present invention relates to the aforementioned method, wherein said patient is a human.

In another aspect, the present invention relates to a method of treating a Bcl-mediated disorder, comprising the step of: administering to a patient in need thereof a therapeutically effective amount of a chemothereutic agent in combination with a therapeutically effective amount of a compound of compound of formula I as defined in the Summary of the Invention.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) nasally; (9) pulmonary; or (10) intrathecally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluene-sulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

Microemulsification technology can improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins are cyclic oligosaccharides, consisting of 6, 7 or 8 glucose units, designated by the Greek letter .alpha., .beta. or .gamma., respectively. Cyclodextrins with fewer than six glucose units are not known to exist. The glucose units are linked by alpha-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17.beta.-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259) and Gramera, et al. (U.S. Pat. No. 3,459,731) described electroneutral cyclodextrins. Other derivatives include cyclodextrins with cationic properties [Parmeter (II), U.S. Pat. No. 3,453,257], insoluble crosslinked cyclodextrins (Solms, U.S. Pat. No. 3,420,788), and cyclodextrins with anionic properties [Parmeter (III), U.S. Pat. No. 3,426,011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127).

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 µm in diameter; large unilamellar vesicles (LUVS) are typically larger than 0.05 µm Oligolamellar large vesicles and multilamellar vesicles have multiple, usually concentric, membrane layers and are typically larger than 0.1 µm. Liposomes with several nonconcentric membranes, i.e., several smaller vesicles contained within a larger vesicle, are termed multivesicular vesicles.

One aspect of the present invention relates to formulations comprising liposomes containing a compound of the present invention, where the liposome membrane is formulated to provide a liposome with increased carrying capacity. Alternatively or in addition, the compound of the present invention may be contained within, or adsorbed onto, the liposome bilayer of the liposome. The compound of the present invention may be aggregated with a lipid surfactant and carried within the liposome's internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about $C_{14}$ to about $C_{20}$). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Liposomes according to the present invention may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic DD, Liposomes from physics to applications, Elsevier Science Publishers BV, Amsterdam, 1993.

For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988).

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

Pharmaceutical Combinations

The invention especially relates to the use of a compound of the formula I (or a pharmaceutical composition comprising a compound of the formula I) in the treatment of one or more of the diseases mentioned herein; wherein the response to treatment is beneficial as demonstrated, for example, by the partial or complete removal of one or more of the symptoms of the disease up to complete cure or remission.

Bcl-2 inhibitors have been shown to be active against a number of cancer cell lines in combination with other anticancer agents and radiation, including, but not limited to, breast cancer (With docetaxel, published PCT application WO 02/097053), prostate cancer (With docetaxel, published PCT application WO 02/097053), head and neck cancer (With docetaxel, published PCT application WO 02/097053), and non small-cell lung cancer (With paclitaxel, Nature (2005) 435, 677-681). In addition to the aforementioned combination chemotherapeutics, small molecule inhibitors of Bcl-2 proteins display synergy with other anticancer agents, including, but not limited to etoposide, doxorubicin, cisplatin, paclitaxel, and radiation (Nature (2005) 435, 677-681).

A compound of formula (I) can also be used in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibittors; mTOR inhibitors, such as RAD001; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies, such as HCD122; heparanase inhibitors; inhibitors of Ras oncogenic isoforms; telomerase inhibitors; proteasome inhibitors; compounds used in the treatment of hematologic malignancies, such as FLUDARABINE; compounds which target, decrease or inhibit the activity of Flt-3, such as PKC412; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics and AUY922; temozolomide (TEMODAL®); kinesin spindle protein inhibitors, such as SB715992 or SB743921 from GlaxoSmithKline, or pentamidine/chlorpromazine from CombinatoRx; PI3K inhibitors, such as BEZ235; RAF inhibitors, such as LGX818 or RAF265; MEK inhibitors such as ARRY142886 from Array PioPharma, AZD6244 from AstraZeneca, PD181461 from Pfizer, leucovorin, EDG binders, antileukemia compounds, ribonucleotide reductase inhibittors, S-adenosylmethionine decarboxylase inhibitors, antiproliferative antibodies or other chemotherapeutic compounds. Further, alternatively or in addition they may be used in combination with other tumor treatment approaches, including surgery, ionizing radiation, photodynamic therapy, implants, e.g. with corticosteroids, hormones, or they may be used as radiosensitizers. Also, in anti-inflammatory and/or antiproliferative treatment, combination with anti-inflammatory drugs is included. Combination is also possible with antihistamine drug substances, bronchodilatatory drugs, NSAID or antagonists of chemokine receptors.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketoconazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. under the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Aminoglutethimide can be administered, e.g., in the form as it is marketed, e.g. under the trademark ORIMETEN. A combination of the invention comprising a chemotherapeutic agent which is an aromatase inhibitor is particularly useful for the treatment of hormone receptor positive tumors, e.g. breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an antiestrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active compound" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating compound" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g. under the trademark HOLOXAN.

The term "histone deacetylase inhibitors" or "HDAC inhibitors" relates to compounds which inhibit the histone deacetylase and which possess antiproliferative activity. This includes compounds such as LDH589 disclosed in WO 02/22577, especially N-hydroxy-3-[4-[[(2-hydroxyethyl)[2-(1H-indol-3-yl)ethyl]-amino]methyl]phenyl]-2E-2-propenamide, N-hydroxy-3-[4-[[[2-(2-methyl-1H-indol-3-yl)-ethyl]-amino]methyl]phenyl]-2E-2-propenamide and pharmaceutically acceptable salts thereof. It further especially includes Suberoylanilide hydroxamic acid (SAHA).

The term "antineoplastic antimetabolite" includes, but is not limited to, 5-Fluorouracil or 5-FU, capecitabine, gemcitabine, DNA demethylating compounds, such as 5-azacytidine and decitabine, methotrexate and edatrexate, and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR.

The term "platin compound" as used herein includes, but is not limited to, carboplatin, cis-platin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity"; or a "protein or lipid phosphatase activity"; or "further anti-angiogenic compounds" as used herein includes, but is not limited to, protein tyrosine kinase and/or serine and/or threonine kinase inhibitors or lipid kinase inhibitors, for example:

a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111;

b) compounds targeting, decreasing or inhibiting the activity of the fibroblast growth factor-receptors (FGFR);

c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-I receptor or its growth factors;

d) compounds targeting, decreasing or inhibiting the activity of the Trk receptor tyrosine kinase family, or ephrin B4 inhibitors;

e) compounds targeting, decreasing or inhibiting the activity of the Axl receptor tyrosine kinase family;

f) compounds targeting, decreasing or inhibiting the activity of the Ret receptor tyrosine kinase;

g) compounds targeting, decreasing or inhibiting the activity of the Kit/SCFR receptor tyrosine kinase, i.e C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib;

h) compounds targeting, decreasing or inhibiting the activity of members of the c-Abl family, their gene-fusion products (e.g. BCR-Abl kinase) and mutants, such as compounds which target decrease or inhibit the activity of c-AbI family members and their gene fusion products, e.g. a N-phenyl-2-pyrimidine-amine derivative, e.g. imatinib or nilotinib (AMN107); PD180970; AG957; NSC 680410; PD173955 from ParkeDavis; or dasatinib (BMS-354825)

i) compounds targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; BEZ235 (a P13K inhibitor) or AT7519 (CDK inhibitor);

j) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin);

k) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herceptin™), cetuximab (Erbitux™), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541; and l) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF.

Further anti-angiogenic compounds include compounds having another mechanism for their activity, e.g. unrelated to protein or lipid kinase inhibition e.g. thalidomide (THALOMID) and TNP-470.

Compounds which target, decrease or inhibit the activity of a protein or lipid phosphatase are e.g. inhibitors of phosphatase 1, phosphatase 2A, or CDC25, e.g. okadaic acid or a derivative thereof.

Compounds which induce cell differentiation processes are e.g. retinoic acid, α- γ- or δ-tocopherol or α- γ- or δ-tocotrienol.

The term cyclooxygenase inhibitor as used herein includes, but is not limited to, e.g. Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA™. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g. compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g. PKC412, TKI258, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino, 17-demethoxygeldanamycin (17AAG), a geldanamycin derivative; other geldanamycin related compounds; radicicol and HDAC inhibitors. An example HSP90 inhibitor is AUY922.

The term "antiproliferative antibodies" as used herein includes, but is not limited to, trastuzumab (Herceptin™), Trastuzumab-DM1, erbitux, bevacizumab (Avastin™) rituximab (Rituxan®), PRO64553 (anti-CD40), 2C4 Antibody and HCD122 antibody (anti-CD40). By antibodies is meant e.g. intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of formula (I) can be used in combination with standard leukemia therapies, especially in combination with therapies used for the treatment of AML. In particular, compounds of formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The term "antileukemic compounds" includes, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate.

Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065, in particular, N-hydroxy-3-[4-[[[2-(2-methyl-1H-indol-3-yl)-ethyl]-amino]-methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt.

Somatostatin receptor antagonists as used herein refers to compounds which target, treat or inhibit the somatostatin receptor such as octreotide, and SOM230 (pasireotide).

Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in *Principles and Practice of Oncology*, Devita et al., Eds., 4$^{th}$ Edition, Vol. 1, pp. 248-275 (1993).

The term "EDG binders" as used herein refers a class of immunosuppressants that modulates lymphocyte recirculation, such as FTY720.

The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL-8 mentioned in Nandy et al., *Acta Oncologica*, Vol. 33, No. 8, pp. 953-961 (1994).

The term "S-adenosylmethionine decarboxylase inhibitors" as used herein includes, but is not limited to the compounds disclosed in U.S. Pat. No. 5,461,076.

Also included are in particular those compounds, proteins or monoclonal antibodies of VEGF disclosed in WO 98/35958, e.g. 1-(4-chloroanilino)-4-(4-pyridylmethyl)phthalazine or a pharmaceutically acceptable salt thereof, e.g. the succinate, or in WO 00/09495, WO 00/27820, WO 00/59509, WO 98/11223, WO 00/27819 and EP 0 769 947; those as described by Prewett et al, *Cancer Res*, Vol. 59, pp. 5209-5218 (1999); Yuan et al., *Proc Natl Acad Sci USA*, Vol. 93, pp. 14765-14770 (1996); Zhu et al., *Cancer Res*, Vol. 58, pp. 3209-3214 (1998); and Mordenti et al., *Toxicol Pathol*, Vol. 27, No. 1, pp. 14-21 (1999); in WO 00/37502 and WO 94/10202; ANGIOSTATIN, described by O'Reilly et al., *Cell*, Vol. 79, pp. 315-328 (1994); ENDOSTATIN, described by O'Reilly et al., *Cell*, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g. rhuMAb and RHUFab, VEGF aptamer e.g. Macugon; FLT-4 inhibitors, FLT-3 inhibitors, VEGFR-2 IgG1 antibody, Angiozyme (RPI 4610) and Bevacizumab (Avastin™)

Photodynamic therapy as used herein refers to therapy which uses certain chemicals known as photosensitizing compounds to treat or prevent cancers. Examples of photodynamic therapy includes treatment with compounds, such as e.g. VISUDYNE and porfimer sodium.

Angiostatic steroids as used herein refers to compounds which block or inhibit angiogenesis, such as, e.g., anecortave, triamcinolone. hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as e.g. fluocinolone, dexamethasone.

"Other chemotherapeutic compounds" include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code nos., generic or trade names may be taken from the actual edition of the standard compendium "The Merck Index" or from databases, e.g. Patents International (e.g. IMS World Publications).

None of the quotations of references made within the present disclosure is to be understood as an admission that the references cited are prior art that would negatively affect the patentability of the present invention.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I, in which $R_3$ is linked to the phenyl ring via an oxygen linker, can be prepared by proceeding as in the following Reaction Scheme I:

Reaction Scheme I:

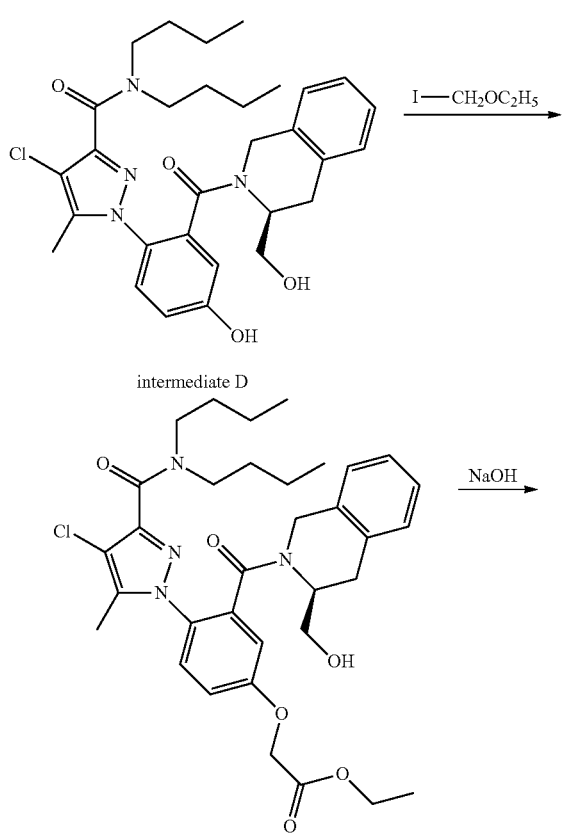

intermediate D

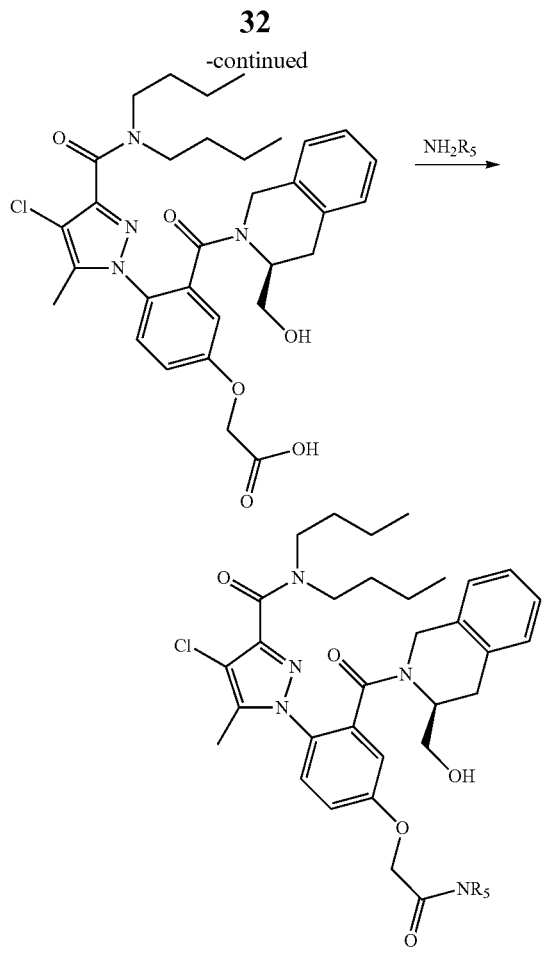

(I)

in which $R_1$, $R_2$, $R_4$ and $R_5$ are as defined for Formula I in the Summary of the Invention. A compound of Formula I can be prepared by reacting intermediate D with I—$CH_2OC_2H_5$ followed by NaOH and reacting the product with $NH_2R_5$ in the presence of a suitable dehydration and cross-linking agent (such as hydroxybenzotriazole and 1-ethyl-3-(3-dimethylaminopropyl)carbodiimide, or the like), a suitable base (such as triethylamine, and the like), and a suitable solvent (such as DCM, and the like). The reaction takes place at about RT and can take up to about 12 hours to complete. For reaction scheme VI, the positions of OH on the phenyl ring of intermediate D can move to be para substituted to the carbonyl group attached to the phenyl ring.

Detailed examples of the synthesis of compounds of Formula I can be found in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Compounds of the formula I can also be modified by appending appropriate functionalities to enhance selective biological properties. Modifications of this kind are known in the art and include those that increase penetration into a given biological system (e.g. blood, lymphatic system, central nervous system, testis), increase bioavailability, increase solubility to allow parenteral administration (e.g. injection, infusion), alter metabolism and/or alter the rate of secretion. Examples of this type of modifications include but are not limited to esterification, e.g. with polyethylene glycols, derivatisation with pivaloyloxy or fatty acid substituents, conversion to carbamates, hydroxylation of aromatic rings and heteroatom substitution in aromatic rings. Wherever compounds of the formula I, and/or N-oxides, tautomers and/or (preferably pharmaceutically acceptable) salts thereof are mentioned, this comprises such modified formulae, while preferably the molecules of the formula I, their N-oxides, their tautomers and/or their salts are meant.

Alternatively, the salt forms of the compounds of the invention can be prepared using salts of the starting materials or intermediates. In view of the close relationship between the novel compounds of the formula I in free form and those in the form of their salts, including those salts that can be used as intermediates, for example in the purification or identification of the novel compounds, any reference to the compounds or a compound of the formula I hereinbefore and hereinafter is to be understood as referring to the compound in free form and/or also to one or more salts thereof, as appropriate and expedient, as well as to one or more solvates, e.g. hydrates.

Salts are formed, for example, as acid addition salts, preferably with organic or inorganic acids, from compounds of formula I with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, malonic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 4-toluenesulfonic acid, 2-naphthalenesulfonic acid, 1,5-naphthalene-disulfonic acid, 2- or 3-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", $3^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:
(a) those of reaction schemes I; and
(b) optionally converting a compound of the invention into a pharmaceutically acceptable salt;
(c) optionally converting a salt form of a compound of the invention to a non-salt form;
(d) optionally converting an unoxidized form of a compound of the invention into a pharmaceutically acceptable N-oxide;
(e) optionally converting an N-oxide form of a compound of the invention to its unoxidized form;
(f) optionally resolving an individual isomer of a compound of the invention from a mixture of isomers;
(g) optionally converting a non-derivatized compound of the invention into a pharmaceutically acceptable prodrug derivative; and
(h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The following intermediates and examples serve to illustrate the invention without limiting the scope thereof. The following abbreviations and methods are used in the descriptions of the examples:

Abreviations:

aq. (aqueous); AcOH (acetic acid); DCM (dichloromethane); DIPEA (diisopropylethylamine); DME (1,2-dimethoxyethane); DMSO (dimethylsulfoxide); EDC (1-(3-dimethylaminopropyl)-3-ethylcarbodiimide hydrochloride); eq (equivalent(s)); Et$_3$N (triethylamine); EtOAc (ethyl acetate); EtOH (ethanol); h (hour(s)); HOBt (1-hydroxybenzotriazole); MeOH (methanol); min (minute(s)); MS (mass spectrometry); N (normality); NMR (nuclear magnetic resonance spectrometry); Rf (retention factor); RT (room temperature); TBDMS (tertiary butyl dimethyl silyl); THF (tetrahydrofuran); and TLC (thin layer chromatography).

HPLC Conditions:

Method A:

Column: Inertsil ODS3V (250×4.6) mm, 5 μm; Mobile phase: A: 0.01M KH$_2$PO$_4$/0.01M KH$_2$PO$_4$ pH adjusted to 6.5; B: ACN; Gradient Information: (T/% B): 0/30, 2/30, 6/85, 16/85, 17/30, 18/30); Flow Rate: 1.0 ml/min; Detection by UV at: 210.0 nm.

Method B:

Column: Inertsil ODS3V (250×4.6) mm, 5 μm; Mobile phase: A: 0.01M KH$_2$PO$_4$/0.01M KH$_2$PO$_4$ pH adjusted to 6.5; B: ACN; Gradient Information: (T/% B): 0/30, 2/30, 6/80, 13/80, 14/30, 15/30); Flow Rate: 1.0 ml/min; Detection by UV at: 210.0 nm.

Method C:

Column: XTerra RP18 (250×4.6) mm, 5 μm; Mobile phase: A: 0.01M KH$_2$PO$_4$/0.01M KH$_2$PO$_4$ pH adjusted to 6.5; B: ACN; Gradient Information: (T/% B): 0/30, 2/30, 6/85, 16/85, 17/30, 18/30); Flow Rate: 1.0 ml/min; Detection by UV at: 210.0 nm.

Method D:

Column: XTerra RP18 (250×4.6) mm, 5 μm; Mobile phase: A: 0.01M KH$_2$PO$_4$/0.01M KH$_2$PO$_4$ pH adjusted to 6.5; B: ACN; Gradient Information: (T/% B): 0/30, 2/30, 6/80, 13/80, 14/30, 15/30); Flow Rate: 1.0 ml/min; Detection by UV at: 210.0 nm.

Method E:

Column: Hypersil BDS C18 (250×4.6) mm, 5 μm; Mobile phase: A: 0.01M KH$_2$PO$_4$/0.01M KH$_2$PO$_4$ pH adjusted to 6.5; B: ACN; Gradient Information: (T/% B): 0/30, 15/50, 18/90, 28/90, 28.10/30); Flow Rate: 0.8 ml/min; Detection by UV at: 260.0 nm.

Method F:

Column: Hypersil BDS C18 (250×4.6) mm, 5 μm; Mobile phase: A: 0.01M ammonium acetate; B: ACN; Gradient Information: (T/% B): 0/30, 15/50, 18/90, 28/90, 28.10/30); Flow Rate: 0.8 ml/min; Detection by UV at: 260.0 nm.

Method G:

Column: XTerra RP18 (250×4.0) mm, 5 μm; Mobile phase: A: 0.01M KH2PO4 (pH 6.5); B: ACN; Gradient Information: (T/% B): 0/30, 2/30, 6/80, 13/80, 14/30, 15/30; Flow Rate: 1.0 ml/min; Detection by UV at: 210.0 nm.

Method H:

Column: Inertsil ODS3V (250×4.6) mm, 5 μm; Mobile phase: A: 0.01M KH2PO4 (pH adjusted to 6.5); B: ACN; Gradient Information: (T/% B): 0/70, 1.5/70, 5/85, 13/85, 14/70, 15/70; Flow Rate: 1.0 ml/min; Detection by UV at: 210.0 nm.

Method I:

Column: XTerra RP18 (250×4.6) mm, 5 μm; Mobile phase: A: 0.01M KH2PO4; B: ACN; Gradient Information: (T/% B): 0/30, 2/30, 6/80, 16/80, 17/30, 18/30; Flow Rate: 1.0 ml/min; Detection by UV at: 210.0 nm.

Method J:

Column: ACES C18 (250×4.6) mm, 5 μm; Mobile phase: A: 0.01M KH2PO4; B: ACN; Gradient Information: (T/% B): 0/30, 2/30, 6/85, 16/85, 17/30, 18/30; Flow Rate: 1.0 ml/min; Detection by UV at: 210.0 nm.

Method K:

Column: Inertsil ODS3V; Mobile phase: A: 0.01M KH2PO4; B: ACN; Gradient Information: (T/% B): 0/50, 1.5/50, 5/80, 13/80, 14/50, 15/50; Flow Rate: 1.0 ml/min; Detection by UV at: 210.0 nm.

Method L:

Column: XTerra RP18 (250×4.6) mm, 5 μm; Mobile phase: A: 0.01M KH2PO4 (pH 6.5); B: ACN; Gradient Information: (T/% B): 0/50, 2/50, 9/85, 16/85, 17/50, 18/50; Flow Rate: 1.0 ml/min; Detection by UV at: 210.0 nm.

Method M:

Column: Symmetry Shield RP18 (150 mm×4.6 mm), 5 μm; Mobile phase: A: 0.01% TFA (aq.); B: ACN; Gradient Information: (T/% B): 0/20, 2/20, 6/85, 13/85, 14/20, 15/20; Flow Rate: 1.0 ml/min; Detection by UV at: 210.0 nm.

NMR Spectra:

1H NMR spectra were recorded on a Varian 400 MHz (Varian Mercury Plus) or 500 MHz (Unity NOVA) spectrometers with DMSO-d$_6$ or CDCl3 as the solvents. Chemical shifts were reported in δ scale using tetramethylsilane (TMS, d 0.00) as internal standard and coupling constants (J) were reported in Hz. The standard abbreviations s, d, t, q, dd, dt and m were used to symbolize singlet, doublet, triplet, quartet, double doublet, doublet of a triplet and multiplet respectively.

Mass Spectra:

The LC-MS and ES-MS spectra were performed on Perkin-Elmer Sciex, model API 3000.

LC-MS Conditions:

Method A:

Regular method in Formic Acid (FA); Column: Cynergi 2.5 μm Max-RP100A (20×4.0) mm; Mobile Phase: A: 0.1% FA (aq.); B: ACN; T/% B: 0/20, 0.5/20, 2.5/95, 4.5/95, 5.0/20; Flow: 1.5 mL/min.

Method B:

Regular method in Ammonium Acetate (AA); Column: Cynergi 2.5 nm Max-RP100A (20×4.0) mm; Mobile Phase:

A: 0.01M Ammonium acetate (aq.); B: ACN; T % B: 0/20, 1.0/20, 2.5/85, 4.0/95, 4.5/20, 5.0/20; Flow: 1.0 mL/min.

Intermediate A (S)-1-(4-amino-2-(3-(hydroxymethyl)-1,2,3,4-tetrahydroisoquinoline-2-carbonyl)phenyl)-N,N-dibutyl-5-methyl-1H-pyrazole-3-carboxamide

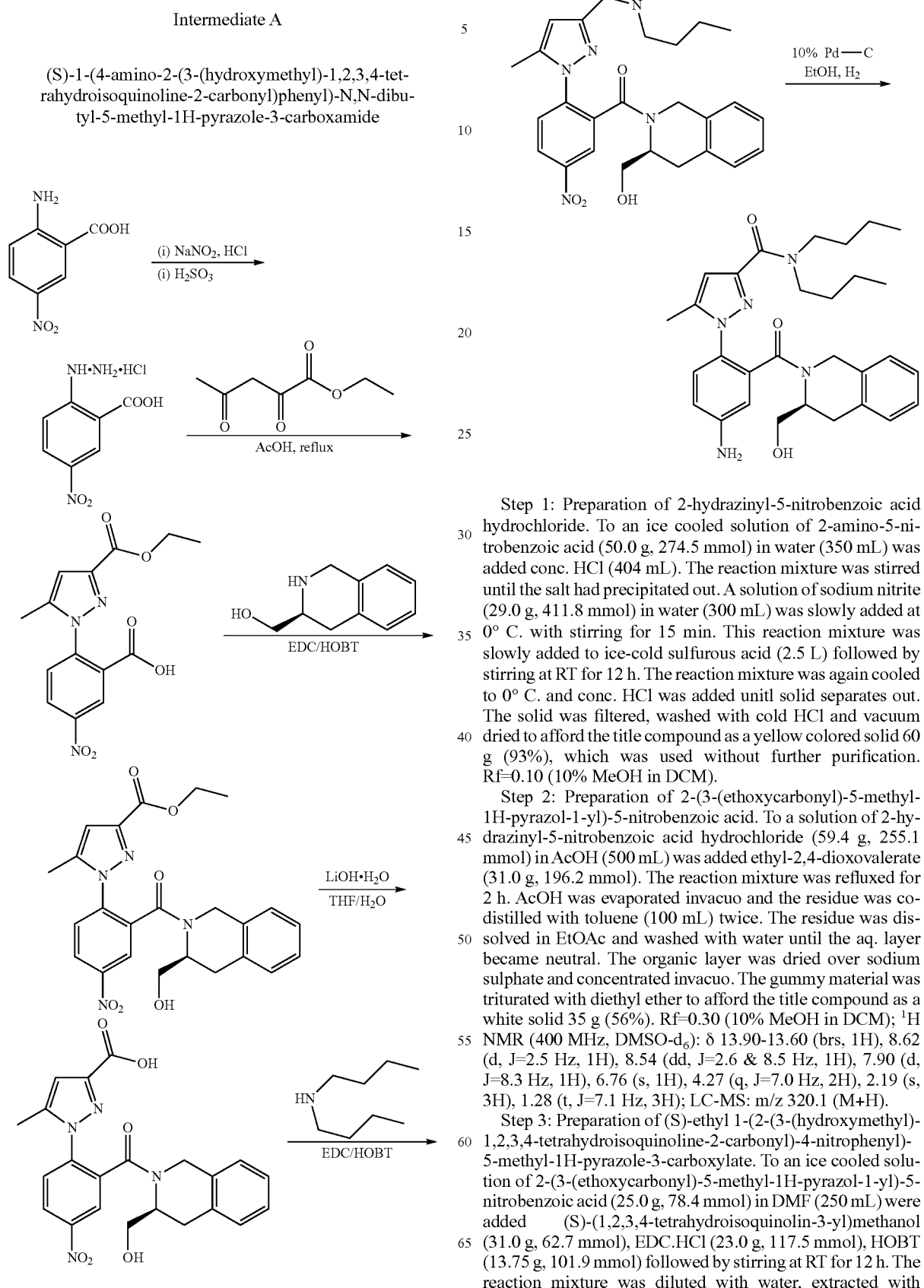

Step 1: Preparation of 2-hydrazinyl-5-nitrobenzoic acid hydrochloride. To an ice cooled solution of 2-amino-5-nitrobenzoic acid (50.0 g, 274.5 mmol) in water (350 mL) was added conc. HCl (404 mL). The reaction mixture was stirred until the salt had precipitated out. A solution of sodium nitrite (29.0 g, 411.8 mmol) in water (300 mL) was slowly added at 0° C. with stirring for 15 min. This reaction mixture was slowly added to ice-cold sulfurous acid (2.5 L) followed by stirring at RT for 12 h. The reaction mixture was again cooled to 0° C. and conc. HCl was added unitl solid separates out. The solid was filtered, washed with cold HCl and vacuum dried to afford the title compound as a yellow colored solid 60 g (93%), which was used without further purification. Rf=0.10 (10% MeOH in DCM).

Step 2: Preparation of 2-(3-(ethoxycarbonyl)-5-methyl-1H-pyrazol-1-yl)-5-nitrobenzoic acid. To a solution of 2-hydrazinyl-5-nitrobenzoic acid hydrochloride (59.4 g, 255.1 mmol) in AcOH (500 mL) was added ethyl-2,4-dioxovalerate (31.0 g, 196.2 mmol). The reaction mixture was refluxed for 2 h. AcOH was evaporated invacuo and the residue was co-distilled with toluene (100 mL) twice. The residue was dissolved in EtOAc and washed with water until the aq. layer became neutral. The organic layer was dried over sodium sulphate and concentrated invacuo. The gummy material was triturated with diethyl ether to afford the title compound as a white solid 35 g (56%). Rf=0.30 (10% MeOH in DCM); $^1$H NMR (400 MHz, DMSO-$d_6$): δ 13.90-13.60 (brs, 1H), 8.62 (d, J=2.5 Hz, 1H), 8.54 (dd, J=2.6 & 8.5 Hz, 1H), 7.90 (d, J=8.3 Hz, 1H), 6.76 (s, 1H), 4.27 (q, J=7.0 Hz, 2H), 2.19 (s, 3H), 1.28 (t, J=7.1 Hz, 3H); LC-MS: m/z 320.1 (M+H).

Step 3: Preparation of (S)-ethyl 1-(2-(3-(hydroxymethyl)-1,2,3,4-tetrahydroisoquinoline-2-carbonyl)-4-nitrophenyl)-5-methyl-1H-pyrazole-3-carboxylate. To an ice cooled solution of 2-(3-(ethoxycarbonyl)-5-methyl-1H-pyrazol-1-yl)-5-nitrobenzoic acid (25.0 g, 78.4 mmol) in DMF (250 mL) were added (S)-(1,2,3,4-tetrahydroisoquinolin-3-yl)methanol (31.0 g, 62.7 mmol), EDC.HCl (23.0 g, 117.5 mmol), HOBT (13.75 g, 101.9 mmol) followed by stirring at RT for 12 h. The reaction mixture was diluted with water, extracted with EtOAc (500 mL×2) twice. The combined organic layers were washed with water (500 mL), brine (100 mL), dried over sodium sulphate and concentrated invacuo. The residue was purified on silica gel (100-200 mesh) to afford the 'off white' title compound 18 g (49%). Rf=0.45 (25% EtOAc in hexane); $^1$H NMR (400 MHz, DMSO-$d_6$): δ 8.70-8.35 (m, 2H), 8.15-7.98 (m, 1H), 7.25-6.95 (m, 4H), 6.82-6.58 (m, 1H), 5.20-3.80 (m, 8H), 3.40-2.40 (m, 2H), 2.38-2.10 (m, 3H), 1.30-0.80 (m, 3H); ES-MS: m/z 465.3 (M+H).

Step 4: Preparation of (S)-1-(2-(3-(hydroxymethyl)-1,2,3,4-tetrahydroisoquinoline-2-carbonyl)-4-nitrophenyl)-5-methyl-1H-pyrazole-3-carboxylic acid. To a solution of (S)-ethyl 1-(2-(3-(hydroxymethyl)-1,2,3,4-tetrahydroisoquinoline-2-carbonyl)-4-nitrophenyl)-5-methyl-1H-pyrazole-3-carboxylate (18.0 g, 38.8 mmol) in THF (30 mL) and water (20 mL) was added lithium hydroxide monohydrate (5.0 g, 116.8 mmol) followed by stirring at RT for 6 h. The reaction mixture was concentrated invacuo, diluted with water (80 mL) and extracted with diethyl ether (100 mL). The aq. layer was cooled to 0° C., acidified up to pH ~4 using 3N HCl and extracted with EtOAc (200 mL×2) twice. The combined organic layers were washed with water (200 mL), brine (100 mL), dried over sodium sulphate and concentrated invacuo. The residue was purified on silica gel (100-200 mesh) to afford the title compound as a white colored solid 14 g (82%). Rf=0.25 (70% EtOAc in hexane); $^1$H NMR (400 MHz, DMSO-$d_6$): δ 12.90-12.50 (brs, 1H), 8.64-8.30 (m, 2H), 8.06-7.72 (m, 1H), 7.24-6.82 (m, 4H), 6.80-6.42 (m, 1H), 5.20-3.80 (m, 6H), 3.40-2.40 (m, 2H), 2.40-2.10 (m, 3H); ES-MS: m/z 437.2 (M+H).

Step 5: Preparation of (S)—N,N-dibutyl-1-(2-(3-(hydroxymethyl)-1,2,3,4-tetrahydroisoquinoline-2-carbonyl)-4-nitrophenyl)-5-methyl-1H-pyrazole-3-carboxamide. To a solution of (S)-1-(2-(3-(hydroxymethyl)-1,2,3,4-tetrahydroisoquinoline-2-carbonyl)-4-nitrophenyl)-5-methyl-1H-pyrazole-3-carboxylic acid (14.0 g, 32.1 mmol) in DMF (150 mL) were added dibutylamine (8.6 mL, 48.2 mmol), EDC.HCl (9.2 g, 48.2 mmol), HOBT (5.63 g, 41.7 mmol) followed by stirring at RT for 12 h. The reaction mixture was diluted with water and extracted with EtOAc (300 mL×2) twice. The combined organic layers were washed with water (300 mL), brine (100 mL), dried over sodium sulphate and concentrated invacuo. The residue was purified on silica gel (100-200 mesh) to afford the title compound as and 'off white' solid 9 g (51%). Rf=0.47 (25% EtOAc in hexane); $^1$H NMR (400 MHz, DMSO-$d_6$): δ 8.62-8.22 (m, 2H), 8.00-7.80 (m, 1H), 7.30-6.84 (m, 4H), 6.60-6.35 (m, 1H), 5.20-3.80 (m, 3H), 3.79-2.40 (m, 9H), 2.38-2.20 (m, 3H), 1.60-0.50 (m, 14H); LC-MS: m/z 548.0 (M+H).

Step 6: Preparation of (S)-1-(4-amino-2-(3-(hydroxymethyl)-1,2,3,4-tetrahydroisoquinoline-2-carbonyl)phenyl)-N,N-dibutyl-5-methyl-1H-pyrazole-3-carboxamide. To a solution of (S)—N,N-dibutyl-1-(2-(3-(hydroxymethyl)-1,2,3,4-tetrahydroisoquinoline-2-carbonyl)-4-nitrophenyl)-5-methyl-1H-pyrazole-3-carboxamide (1.1 g, 2.0 mmol) in EtOH (10 mL) was added 10% Pd—C(0.04 g) followed by stirring under $H_2$ balloon pressure at RT for 5 h. The reaction mixture was filtered through celite, the bed was washed with EtOH (20 mL) and the filtrate was concentrated invacuo. The residue was purified on silica gel (100-200 mesh) to afford the title compound as an 'off white' solid 0.8 g (77%). Rf=0.33 (40% EtOAc in hexane); $^1$H NMR (400 MHz, DMSO-$d_6$): δ 7.30-6.82 (m, 5H), 6.80-6.15 (m, 3H), 5.72-5.50 (m, 2H, $D_2O$ exchangeable), 5.20-4.78 (m, 1H, $D_2O$ exchangeable), 4.90-4.00 (m, 2H), 4.00-2.22 (m, 9H), 2.20-2.00 (m, 3H), 1.60-0.60 (m, 14H); LC-MS: m/z 518.3 (M+H); HPLC: 98.64% (RT=5.997 min., method B).

Intermediate B (S)-1-(4-amino-2-(3-(((tert-butyldimethylsilyl)oxy)methyl)-1,2,3,4-tetrahydroisoquinoline-2-carbonyl)phenyl)-N,N-dibutyl-5-methyl-1H-pyrazole-3-carboxamide

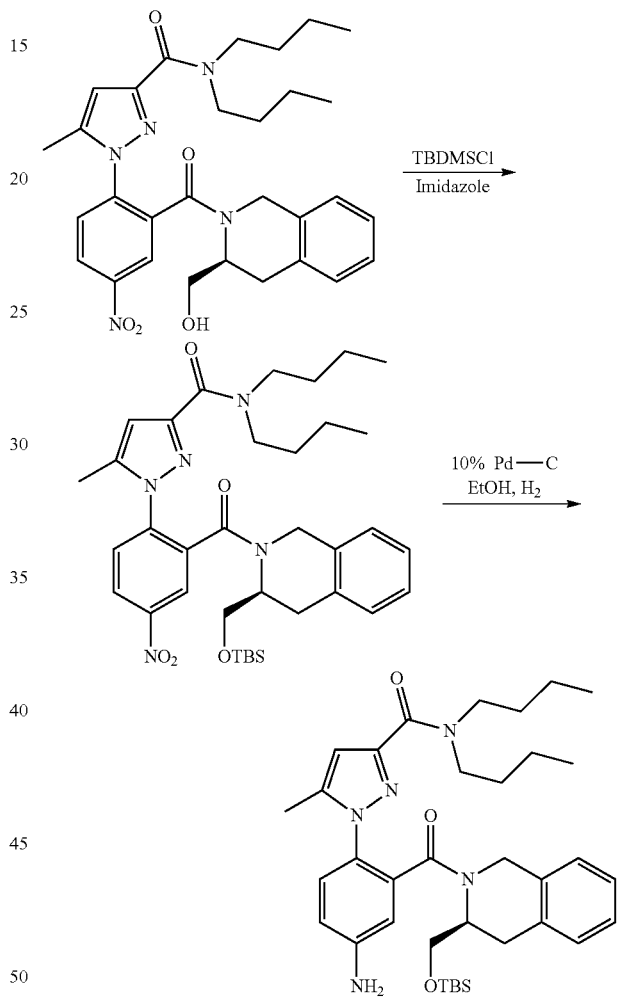

Step 1: Preparation of (S)—N,N-dibutyl-1-(2-(3-(((tert-butyldimethylsilyl)-oxy)methyl)-1,2,3,4-tetrahydroisoquinoline-2-carbonyl)-4-nitrophenyl)-5-methyl-1H-pyrazole-3-carboxamide. To a solution of (S)—N,N-dibutyl-1-(2-(3-(hydroxymethyl)-1,2,3,4-tetrahydroisoquinoline-2-carbonyl)-4-nitrophenyl)-5-methyl-1H-pyrazole-3-carboxamide (9.0 g, 16.4 mmol) in DCM (150 mL) were added TBDMS-chloride (2.98 g, 19.7 mmol), imidazole (2.23 g, 32.9 mmol) followed by stirring at RT for 12 h. The reaction mixture was diluted with water and extracted with EtOAc (300 mL×2), twice. The combined organic layers were washed with water (300 mL), brine (100 mL), dried over sodium sulphate and concentrated invacuo. The residue was purified on silica gel (100-200 mesh) to afford the title compound as a liquid 7 g (64%). Rf=0.74 (25% EtOAc in hexane);

$^1$H NMR (400 MHz, DMSO-d$_6$): δ 8.60-8.20 (m, 2H), 8.05-7.80 (m, 1H), 7.40-6.80 (m, 4H), 6.60-6.30 (m, 1H), 5.10-3.84 (m, 4H), 3.82-2.40 (m, 7H), 2.40-2.20 (m, 3H), 1.60-0.55 (m, 23H), 0.05--0.40 (m, 6H); LC-MS: m/z 662.4 (M+H).

Step 2: Preparation of (S)-1-(4-amino-2-(3-(((tert-butyldimethylsilyl)-oxy)methyl)-1,2,3,4-tetrahydroisoquinoline-2-carbonyl)phenyl)-N,N-dibutyl-5-methyl-1H-pyrazole-3-carboxamide. To a solution of (S)—N,N-dibutyl-1-(2-(3-(((tert-butyldimethylsilyl)-oxy)methyl)-1,2,3,4-tetrahydroisoquinoline-2-carbonyl)-4-nitrophenyl)-5-methyl-1H-pyrazole-3-carboxamide (3.0 g, 4.5 mmol) in EtOH (50 mL) was added 10% Pd—C(0.3 g) followed by stirring under H$_2$ balloon pressure at RT for 3 h. The reaction mixture was filtered through celite, the bed was washed with EtOH (150 mL) and the filtrate was concentrated invacuo. The residue was purified on silica gel (100-200 mesh) to afford the title compound as an 'off white' solid 2.0 g (69%). Rf=0.45 (25% EtOAc in hexane); $^1$H NMR (400 MHz, DMSO-d$_6$): δ 7.40-6.82 (m, 5H), 6.80-6.20 (m, 3H), 5.74-5.50 (m, 2H), 5.10-4.00 (m, 2H), 3.99-2.20 (m, 9H), 2.20-2.00 (m, 3H), 1.60-0.58 (m, 23H), 0.00--0.04 (m, 6H); LC-MS: m/z 632.6 (M+H).

Intermediate C (S)-1-(4-bromo-2-(3-(((tert-butyldimethylsilyl)oxy)methyl)-1,2,3,4-tetrahydro-isoquinoline-2-carbonyl)phenyl)-N,N-dibutyl-5-methyl-1H-pyrazole-3-carboxamide

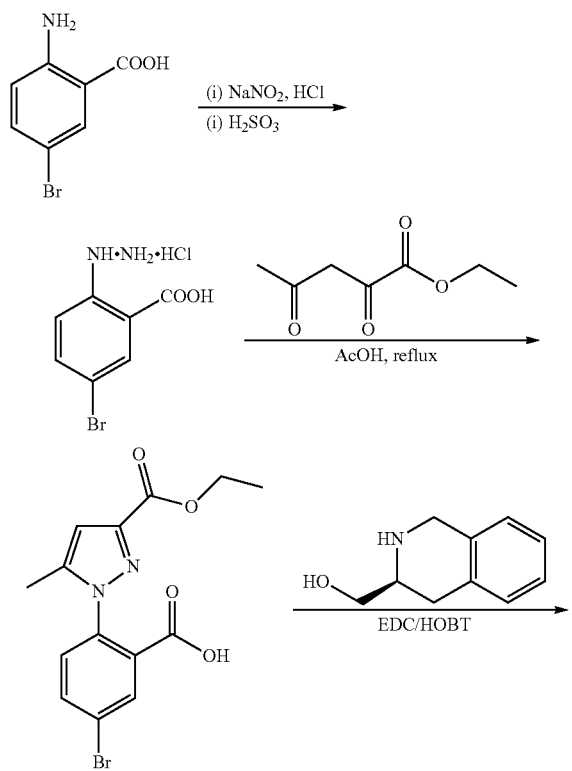

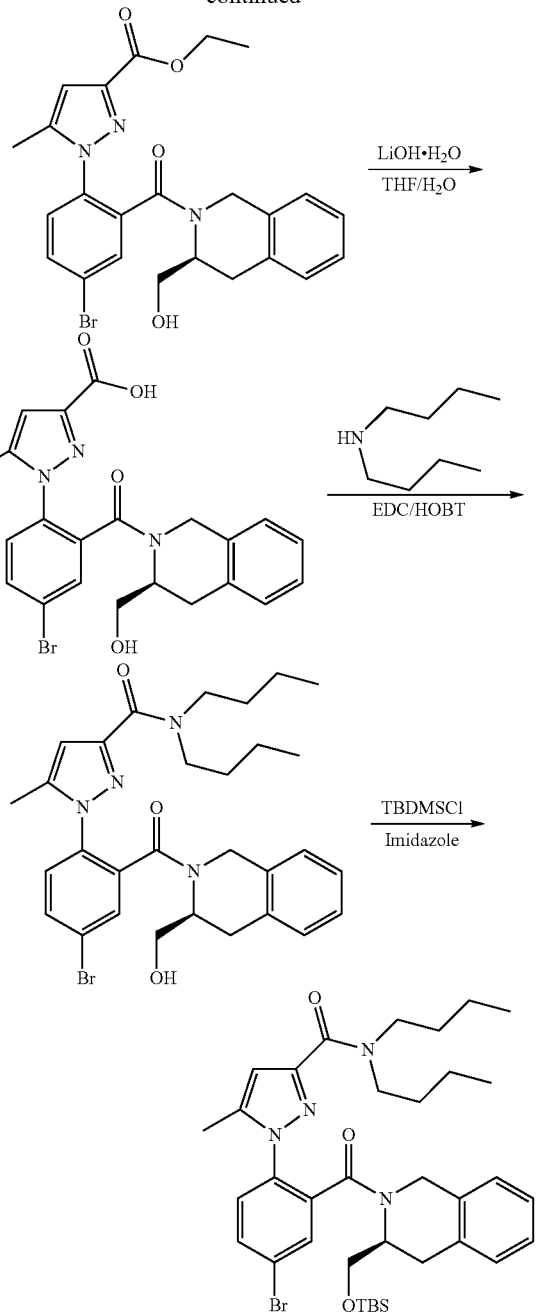

Step 1: Preparation of 5-bromo-2-hydrazinylbenzoic acid hydrochloride. To a suspension of 2-amino-5-bromobenzoic acid (50.0 g, 231.5 mmol) in conc. HCl (250 mL) at −10° C. was added a solution of sodium nitrite (23.92 g, 347.2 mmol) in water (250 mL), slowly, followed by stirring for 2 h. To this reaction mixture was slowly added a solution of stannous chloride (130.50 g, 225.6 mmol) in conc. HCl (125 mL) with continued stirring at RT for 12 h. The reaction mixture was filtered, the residue washed with the minimum amount of water and vacuum dried to afford the title compound as and 'off white' solid 61 g (100%), which was used for next step without further purification. Rf=0.10 (ethyl acetate); $^1$H NMR (400 MHz, DMSO-d$_6$): δ 11.60-9.60 (brs, 3H), 7.93 (d, J=2.4 Hz, 1H), 7.72 (dd, J=2.4 & 8.8 Hz, 1H), 7.12 (d, J=8.8 Hz, 1H); ES-MS: m/z 229.1 (M−H).

Step 2: Preparation of 5-bromo-2-(3-(ethoxycarbonyl)-5-methyl-1H-pyrazol-1-yl)benzoic acid. To a solution of 5-bromo-2-hydrazinylbenzoic acid hydrochloride (60.0 g, 225.6 mmol) in AcOH (600 mL) was added ethyl-2,4-dioxovalerate (35.67 g, 225.6 mmol) followed by refluxing for 3 h. AcOH was evaporated invacuo and the residue was co-distilled with toluene (100 mL), twice. The residue was dissolved in EtOAc and washed with water until the aq. layer became neutral. The organic layer was dried over sodium sulphate and concentrated invacuo. The gummy material was triturated with diethyl ether to afford the title compound as a brown colored oil 80 g (100%), which was used without further purification for the next step. Rf=0.23 (10% MeOH in DCM); $^1$H NMR (400 MHz, DMSO-d$_6$): δ 13.80-12.80 (brs, 1H), 8.08 (d, J=1.9 Hz, 1H), 7.96 (dd, J=2.4&8.3 Hz, 1H), 7.53 (d, J=8.3 Hz, 1H), 6.70 (s, 1H), 4.26 (q, J=7.2 Hz, 2H), 2.13 (s, 3H), 1.28 (t, J=7.1 Hz, 3H); ES-MS: m/z 353.1 (M+H).

Step 3: Preparation of (S)-ethyl 1-(4-bromo-2-(3-(hydroxymethyl)-1,2,3,4-tetrahydroisoquinoline-2-carbonyl)phenyl)-5-methyl-1H-pyrazole-3-carboxylate. To an ice cooled solution of 5-bromo-2-(3-(ethoxycarbonyl)-5-methyl-1H-pyrazol-1-yl)benzoic acid (45.0 g, 127.8 mmol) in DCM (450 mL) were added (S)-(1,2,3,4-tetrahydroisoquinolin-3-yl)methanol (20.8 g, 102.27 mmol), HATU (72.7 g, 191.2 mmol), DIPEA (55.7 mL, 319.6 mmol) followed by stirring at RT for 12 h. The reaction mixture was diluted with DCM (750 mL), washed with water (500 mL), brine (100 mL), dried over sodium sulphate and concentrated invacuo. The residue was purified on silica gel (100-200 mesh) to afford the the title compound as a liquid 50 g (79%). Rf=0.44 (55% EtOAc in hexane); $^1$H NMR (400 MHz, DMSO-d$_6$): δ 8.00-7.40 (m, 3H), 7.30-7.00 (m, 4H), 6.80-6.40 (m, 1H), 5.10-3.80 (m, 7H), 3.50-2.40 (m, 3H), 2.40-2.10 (m, 3H), 1.30-1.00 (m, 3H); ES-MS: m/z 498.2 (M+H).

Step 4: Preparation of (S)-1-(4-bromo-2-(3-(hydroxymethyl)-1,2,3,4-tetrahydroisoquinoline-2-carbonyl)phenyl)-5-methyl-1H-pyrazole-3-carboxylic acid. To a solution of (S)-ethyl 1-(4-bromo-2-(3-(hydroxymethyl)-1,2,3,4-tetrahydroisoquinoline-2-carbonyl)phenyl)-5-methyl-1H-pyrazole-3-carboxylate (50.0 g, 100.6 mmol) in THF (80 mL) and water (20 mL) was added lithium hydroxide monohydrate (21.1 g, 503.0 mmol) followed by stirring at RT for 12 h. The reaction mixture was concentrated invacuo, diluted with water (80 mL) and extracted with diethyl ether (100 mL). The aq. layer was cooled to 0° C., acidified up to pH ~4 using 3N HCl and extracted with EtOAc (200 mL×2), twice. The combined organic layers were washed with water (200 mL), brine (100 mL), dried over sodium sulphate and concentrated invacuo. The residue was purified on silica gel (100-200 mesh) to afford the title compound as a pale yellow solid, 40 g (crude). Rf=0.10 (30% EtOAc in hexane); $^1$H NMR (400 MHz, DMSO-d$_6$): δ 12.80-11.80 (m, 1H), 8.15-7.40 (m, 3H), 7.30-6.90 (m, 4H), 6.70-6.30 (m, 1H), 5.10-3.70 (m, 5H), 3.50-2.40 (m, 3H), 2.38-2.10 (m, 3H); ES-MS: m/z 470.5 (M+H).

Step 5: Preparation of (S)-1-(4-bromo-2-(3-(hydroxymethyl)-1,2,3,4-tetrahydroisoquinoline-2-carbonyl)phenyl)-N,N-dibutyl-5-methyl-1H-pyrazole-3-carboxamide. To a solution of (S)-1-(4-bromo-2-(3-(hydroxymethyl)-1,2,3,4-tetrahydroisoquinoline-2-carbonyl)phenyl)-5-methyl-1H-pyrazole-3-carboxylic acid (10.0 g, 21.3 mmol) in DMF (100 mL) were added dibutylamine (3.7 mL, 21.3 mmol), EDC.HCl (6.1 g, 31.9 mmol), HOBT (3.3 g, 21.3 mmol) followed by stirring at RT for 12 h. The reaction mixture was diluted with water, extracted with EtOAc (100 mL×2), twice. The combined organic layers were washed with water (100 mL), brine (50 mL), dried over sodium sulphate and concentrated invacuo. The residue was purified on silica gel (100-200 mesh) to afford the title compound as a hygroscopic solid, 4.5 g (36%). Rf=0.44 (55% EtOAc in hexane); $^1$H NMR (400 MHz, DMSO-d$_6$): δ 8.00-7.40 (m, 3H), 7.30-6.80 (m, 4H), 6.50-6.20 (m, 1H), 5.10-4.00 (m, 3H), 4.00-2.40 (m, 9H), 2.40-2.00 (m, 3H), 1.60-0.50 (m, 14H); LC-MS: m/z 581.4 (M+H); HPLC: 90.74% (RT=9.216 min., method C).

Step 6: Preparation of (S)-1-(4-bromo-2-(3-(((tert-butyldimethylsilyl)-oxy)methyl)-1,2,3,4-tetrahydro-isoquinoline-2-carbonyl)phenyl)-N,N-dibutyl-5-methyl-1H-pyrazole-3-carboxamide. To a solution of (S)-1-(4-bromo-2-(3-(hydroxymethyl)-1,2,3,4-tetrahydroisoquinoline-2-carbonyl)phenyl)-N,N-dibutyl-5-methyl-1H-pyrazole-3-carboxamide (3.0 g, 5.2 mmol) in DCM (30 mL) were added TBDMS-chloride (0.93 g, 6.2 mmol), imidazole (0.70 g, 10.3 mmol) followed by stirring at RT for 5 h. The reaction mixture was diluted with water, extracted with EtOAc (100 mL×2), twice. The combined organic layers were washed with water (100 mL), brine (50 mL), dried over sodium sulphate and concentrated invacuo. The residue was purified on silica gel (100-200 mesh) to afford the title compound as a liquid 3.0 g (83%). Rf=0.66 (50% EtOAc in hexane); $^1$H NMR (400 MHz, DMSO-d$_6$): δ 8.00-7.40 (m, 3H), 7.30-6.60 (m, 4H), 6.55-6.20 (m, 1H), 5.00-4.10 (m, 2H), 4.10-2.40 (m, 6H), 2.40-2.00 (m, 6H), 1.60-0.50 (m, 23H), 0.20-−0.40 (m, 6H); LC-MS: m/z 695.3 (M+H).

Intermediate D

4-Chloro-1-[4-hydroxy-2-((S)-3-hydroxymethyl-3,4-dihydro-1H-isoquinoline-2-carbonyl)-phenyl]-5-methyl-1H-pyrazole-3-carboxylic acid dibutylamide

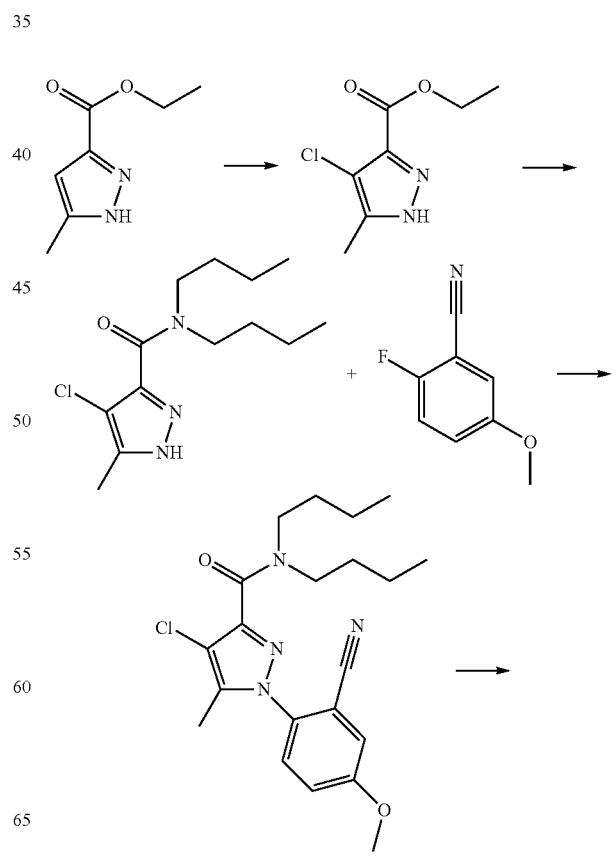

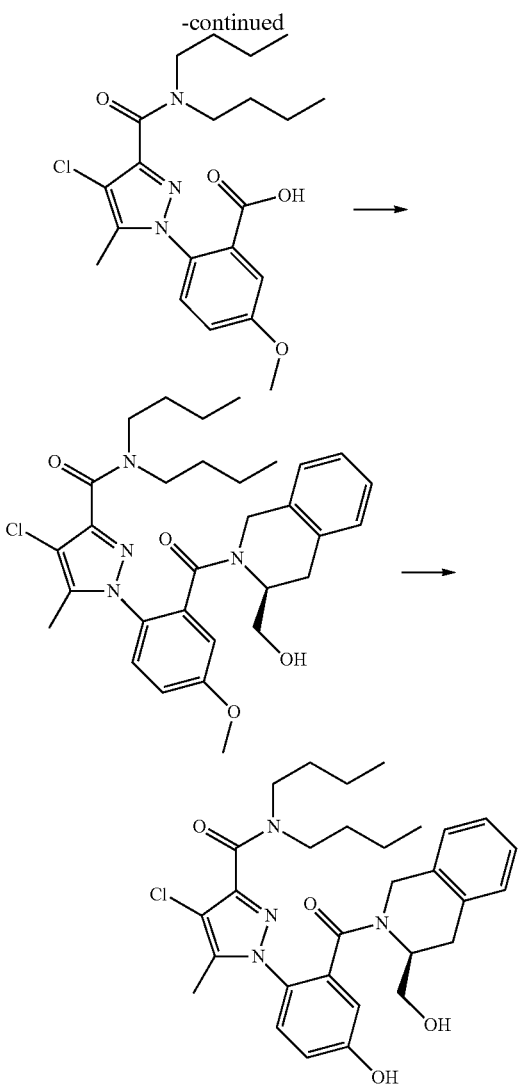

Step 1: Preparation of 4-Chloro-5-methyl-1H-pyrazole-3-carboxylic acid ethyl ester. A mixture of 5-methyl-1H-pyrazole-3-carboxylic acid ethyl ester (4.45 g, 28.9 mmol) and N-chlorosuccinimide (5.01 g, 37.5 mmol) in dimethylformamide (60 mL) was stirred for 24 hours at ambient temperature. The reaction was then concentrated down and purified by eluting through a silica gel column with a 0 to 100% ethyl acetate/heptane gradient to afford the title compound (5.2 g, 96% yield) as a white solid. MS (ESI) [m/e, (M+H)$^+$]=189.3. $^1$H NMR (400 MHz, chloroform-d) δ ppm 9.39 (br. s., 1H), 4.44 (q, J=7.1 Hz, 2H), 2.35 (s, 3H), 1.43 (t, J=7.1 Hz, 3H).

Step 2: Preparation of 4-Chloro-5-methyl-1H-pyrazole-3-carboxylic acid dibutylamide. To a stirred solution of dibutylamine (13 mL, 76 mmol) in dichloromethane (250 mL) under nitrogen atmosphere was added trimethylaluminium (38 mL, 2M in toluene, 76 mmol). The mixture was stirred at ambient temperature for 30 minutes. (4-Chloro-5-methyl-1H-pyrazole-3-carboxylic acid ethyl ester (4.8 g, 25 mmol) in dichloromethane (30 mL) was added dropwise to the mixture. The reaction was stirred for 12 hours under a nitrogen atmosphere. The mixture was poured into saturated Rochelle salt solution slowly and stirred at ambient temperature for 2 hours. The organic layer was collected. The aqueous layer was extracted with dichloromethane and combined with the organic layer. The organic phase was brine-washed, dried over sodium sulfate, filtered, concentrated down, and dried. The residue was purified by eluting through a silica gel column with a 0 to 100% ethyl acetate/heptane gradient to afford the title compound (4.7 g, 68% yield) as a clear oil. MS (ESI) [m/e, (M+H)$^+$]=272.4. $^1$H NMR (400 MHz, chloroform-d) δ ppm 3.50 (t, J=7.5 Hz, 2H), 3.37 (t, J=7.5 Hz, 2H), 2.28 (s, 3H), 1.64 (quin, J=7.5 Hz, 2H), 1.44-1.55 (m, 2H), 1.30-1.43 (m, 2H), 1.10-1.22 (m, 2H), 0.97 (t, J=8.0 Hz, 3H), 0.82 (t, J=7.3 Hz, 3H).

Step 3: Preparation of 4-Chloro-1-(2-cyano-4-methoxy-phenyl)-5-methyl-1H-pyrazole-3-carboxylic acid dibutylamide. A mixture of 4-chloro-5-methyl-1H-pyrazole-3-carboxylic acid dibutylamide (1.5 g, 5.5 mmol), 2-fluoro-5-methoxybenzonitrile (1.1 g, 7.2 mmol), and cesium carbonate (1.8 g, 5.5 mmol) in dimethylformamide (5 mL) was microwaved at 130° C. for 30 minutes. The solvent was removed in vacuo. The crude material was eluted through a silica gel column with a 0 to 70% ethyl acetate/heptane gradient to afford the title compound (1.3 g, 59% yield) as a white solid. MS (ESI) [m/e, (M+H)$^+$]=403.5. $^1$H NMR (400 MHz, chloroform-d) δ ppm 7.32 (d, J=8.5 Hz, 1H), 7.18-7.22 (m, 1H), 7.12-7.18 (m, 1H), 3.84 (s, 3H), 3.41-3.51 (m, 2H), 3.32-3.41 (m, 2H), 2.15 (s, 3H), 1.54-1.66 (m, 2H), 1.48 (qd, J=7.7, 7.5 Hz, 2H), 1.26-1.40 (m, 2H), 1.17 (ddd, J=14.9, 7.4, 7.3 Hz, 2H), 0.89 (t, J=7.3 Hz, 3H), 0.77 (t, J=7.3 Hz, 3H).

Step 4: Preparation of 2-(4-Chloro-3-dibutylcarbamoyl-5-methyl-pyrazol-1-yl)-5-methoxy-benzoic acid. A mixture of 4-Chloro-1-(2-cyano-4-methoxy-phenyl)-5-methyl-1H-pyrazole-3-carboxylic acid dibutylamide (1.3 g, 3.2 mmol) and potassium hydroxide (1.2 g, 21 mmol) in ethanol (5 mL) and water (5 mL) was microwaved at 150° C. for 90 minutes. The pH was adjusted to about 5 with aqueous HCl solution (15 N). The solvent was removed in vacuo. The crude material was eluted through a silica gel column with a 10 to 100% ethyl acetate/heptane and then 1 to 20% methanol/methylene chloride gradient to afford the title compound (0.53 g, 39% yield) as a white solid. MS (ESI) [m/e, (M+H)$^+$]=422.4.

Step 5: Preparation of 4-Chloro-1-[2-((S)-3-hydroxymethyl-3,4-dihydro-1H-isoquinoline-2-carbonyl)-4-methoxy-phenyl]-5-methyl-1H-pyrazole-3-carboxylic acid dibutylamide. To a stirred solution of 2-(4-chloro-3-dibutylcarbamoyl-5-methyl-pyrazol-1-yl)-5-methoxy-benzoic acid (0.35 g, 0.82 mmol) and (S)-(1,2,3,4-tetrahydroisoquinolin-3-yl)methanol (0.13 g, 0.82 mmol) in dichloromethane (8 mL) under nitrogen atmosphere was added 1-ethyl-3-(3-dimethylaminopropyl)carbodiimide (0.16 g, 0.82 mmol) and hydroxybenzotriazole (0.13 g, 0.82 mmol). The mixture was stirred at ambient temperature for 5 minutes. Triethylamine (0.34 mL, 2.5 mmol) was added to the mixture. The reaction was stirred for 60 hours at ambient temperature. The mixture was washed with water and purified by eluting through a silica gel column with a 10 to 100% ethyl acetate/heptane gradient to afford the title compound (21 mg, 4.5% yield). MS (ESI) [m/e, (M+H)$^+$]=567.3. $^1$H NMR (400 MHz, chloroform-d) δ ppm 6.75-7.36 (m, 7H), 4.13-5.41 (m, 4H), 3.80-3.96 (m, 3H), 2.51-3.71 (m, 8H), 2.17-2.32 (m, 3H), 1.48-1.68 (m, 4H), 1.19-1.44 (m, 4H), 0.70-0.97 (m, 6H).

Step 6: 4-Chloro-1-[4-hydroxy-2-((S)-3-hydroxymethyl-3,4-dihydro-1H-isoquinoline-2-carbonyl)-phenyl]-5-methyl-1H-pyrazole-3-carboxylic acid dibutylamide. A mixture of 4-chloro-1-[2-((S)-3-hydroxymethyl-3,4-dihydro-1H-isoquinoline-2-carbonyl)-4-methoxy-phenyl]-5-methyl-1H-pyrazole-3-carboxylic acid dibutylamide (40 mg, 0.071 mmol) and aluminium chloride (75 mg, 0.56 mmol) was stirred in ethanethiol (0.052 mL, 0.71 mmol) and dichloromethane (0.5 mL) for 12 hours at ambient temperature under a nitrogen atmosphere. The mixture was added with water and extracted with 1:4 methanol:methylene chloride. The organic layer was removed in vacuo. After eluting through a short pad of silica gel column and C18 column, the crude material was purified by HPLC to afford the title compound (9 mg, 33% yield). MS (ESI) [m/e, (M+H)$^+$]=553.5. $^1$H NMR (400 MHz, DMSO-d$_6$) δ ppm 6.66-7.50 (m, 7H), 2.03-5.08 (m, 14H), 0.53-1.62 (m, 14H).

Intermediate E

1-[5-Hydroxy-2-((S)-3-hydroxymethyl-3,4-dihydro-1H-isoquinoline-2-carbonyl)-phenyl]-5-methyl-1H-pyrazole-3-carboxylic acid dibutylamide

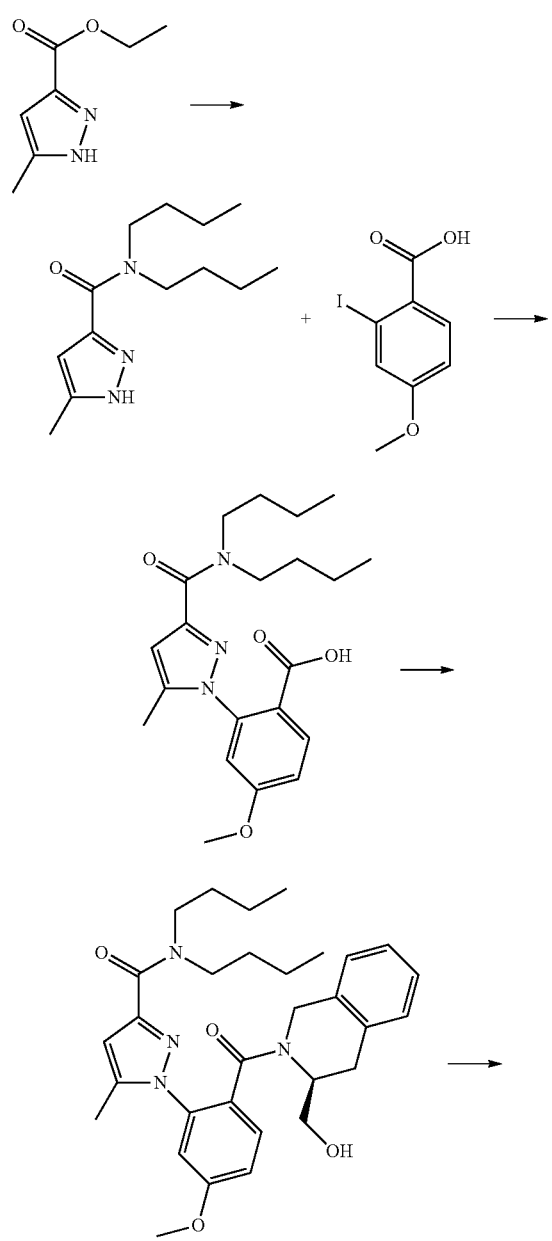

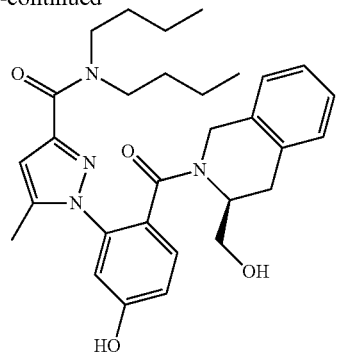

Step 1: Preparation of 5-Methyl-1H-pyrazole-3-carboxylic acid dibutylamide. Following Preparation of Intermediate D/Step 2, the title compound (6 g, 65%) was prepared from 5-methyl-1H-pyrazole-3-carboxylic acid ethyl ester. MS (ESI) [m/e, (M+H)$^+$]=238.1. $^1$H NMR (400 MHz, chloroform-d) δ ppm 6.29 (s, 1H), 3.59 (t, J=7.5 Hz, 2H), 3.38-3.51 (m, 2H), 2.32 (s, 3H), 1.47-1.74 (m, 4H), 1.17-1.47 (m, 4H), 0.76-1.03 (m, 6H).

Step 2: Step 2: 2-(3-Dibutylcarbamoyl-5-methyl-pyrazol-1-yl)-4-methoxy-benzoic acid. A mixture of 5-methyl-1H-pyrazole-3-carboxylic acid dibutylamide (0.85 g, 3.6 mmol), 2-iodo-4-methoxybenzoic acid (1.0 g, 3.6 mmol), copper iodide (0.14 g, 0.72 mmol), cesium carbonate (1.2 g, 3.6 mmol), and trans-dimethylaminecyclohexane (0.23 mL, 1.44 mmol) in dioxane (5 mL) was microwaved at 120° C. for 15 minutes. Diluted with ethyl acetate, the crude material was eluted through a silica gel column with a 0 to 100% ethyl acetate/heptane and then 0 to 20% methanol/methylene chloride gradient to afford the title compound (0.43 g, 31% yield). MS (ESI) [m/e, (M+H)$^+$]=388.5.

Step 3: 1-[2-((S)-3-Hydroxymethyl-3,4-dihydro-1H-isoquinoline-2-carbonyl)-5-methoxy-phenyl]-5-methyl-1H-pyrazole-3-carboxylic acid dibutylamide. Following Preparation of Intermediate D/Step 5, the title compound (610 mg, 29%) was prepared from 2-(3-dibutylcarbamoyl-5-methyl-pyrazol-1-yl)-4-methoxy-benzoic acid. MS (ESI) [m/e, (M+H)$^+$]=533.3. $^1$H NMR (400 MHz, chloroform-d) δ ppm 6.81-7.33 (m, 7H), 5.95-6.40 (m, 1H), 4.28-5.62 (m, 4H), 3.83-3.96 (m, 3H), 2.66-3.81 (m, 7H), 2.01-2.38 (m, 3H), 1.10-1.65 (m, 8H), 0.76-1.01 (m, 6H).

Example 1

[4-(4-Chloro-3-dibutylcarbamoyl-5-methyl-pyrazol-1-yl)-3-((S)-3-hydroxymethyl-3,4-dihydro-1H-isoquinoline-2-carbonyl)-phenoxy]-acetic acid ethyl ester

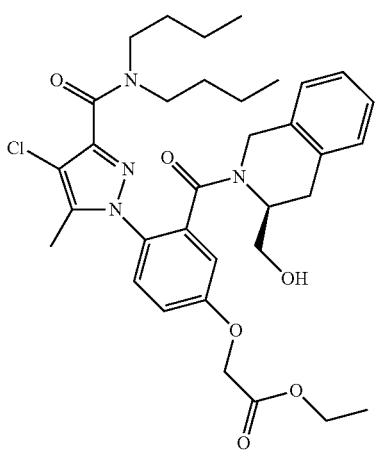 [SMILES: CCCCN(CCCC)C(=O)c1nn(-c2ccc(OCC(=O)OCC)cc2C(=O)N2Cc3ccccc3C[C@H]2CO)c(C)c1Cl]

A mixture of 4-chloro-1-[4-hydroxy-2-((S)-3-hydroxymethyl-3,4-dihydro-1H-isoquinoline-2-carbonyl)-phenyl]-5-methyl-1H-pyrazole-3-carboxylic acid dibutylamide (intermediate D, 170 mg, 0.31 mmol), ethyl 2-iodoacetate (99 mg, 0.46 mmol), potassium carbonate (13 mg, 0.092 mmol), and triethylamime (0.085 mL, 0.62 mmol) was stirred in acetonitrile (3 mL) at ambient temperature for 12 hours. The solvent was removed in vacuo. The crude material was purified by eluting through a silica gel column with a 10 to 100% ethyl acetate/heptane gradient to afford the title compound (15 mg, 7.6% yield). MS (ESI) [m/e, (M+H)$^+$]=639.3. $^1$H NMR (400 MHz, chloroform-d) δ ppm 6.73-7.39 (m, 7H), 2.51-5.41 (m, 17H), 2.16-2.41 (m, 3H), 0.68-1.70 (m, 16H).

Example 2

[4-(4-Chloro-3-dibutylcarbamoyl-5-methyl-pyrazol-1-yl)-3-((S)-3-hydroxymethyl-3,4-dihydro-1H-isoquinoline-2-carbonyl)-phenoxy]-acetic acid

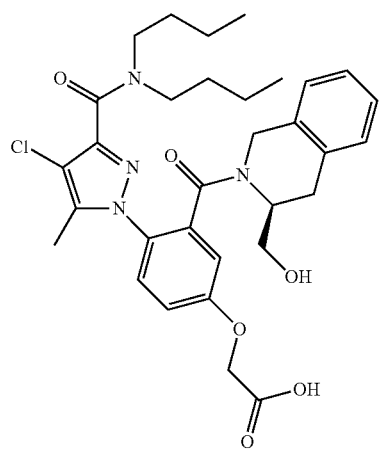 [SMILES: CCCCN(CCCC)C(=O)c1nn(-c2ccc(OCC(=O)O)cc2C(=O)N2Cc3ccccc3C[C@H]2CO)c(C)c1Cl]

A solution of [4-(4-chloro-3-dibutylcarbamoyl-5-methyl-pyrazol-1-yl)-3-((S)-3-hydroxymethyl-3,4-dihydro-1H-isoquinoline-2-carbonyl)-phenoxy]-acetic acid ethyl ester (10 mg, 0.016 mmol) in sodium hydroxide (2N, 0.039 mL) and methanol (0.1 mL) was stirred at ambient temperature for 12 hours. Added aqueous HCl solution until pH is about 5. The crude material was purified by HPLC to afford the title compound (1.9 mg, 20% yield). MS (ESI) [m/e, (M+H)$^+$]=611.5. $^1$H NMR (400 MHz, chloroform-d) δ ppm 6.78-7.37 (m, 7H), 4.08-5.51 (m, 5H), 2.33-3.75 (m, 8H), 2.13-2.33 (m, 3H), 0.60-1.72 (m, 14H).

Example 3

4-Chloro-1-[2-((S)-3-hydroxymethyl-3,4-dihydro-1H-isoquinoline-2-carbonyl)-4-phenylcarbamoylmethoxy-phenyl]-5-methyl-1H-pyrazole-3-carboxylic acid dibutylamide

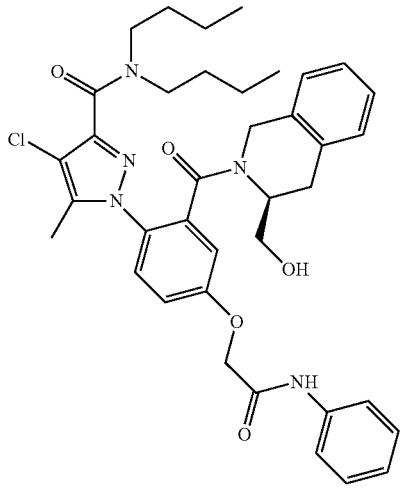 [SMILES: CCCCN(CCCC)C(=O)c1nn(-c2ccc(OCC(=O)Nc3ccccc3)cc2C(=O)N2Cc3ccccc3C[C@H]2CO)c(C)c1Cl]

To a stirred solution of [4-(4-chloro-3-dibutylcarbamoyl-5-methyl-pyrazol-1-yl)-3-((S)-3-hydroxymethyl-3,4-dihydro-1H-isoquinoline-2-carbonyl)-phenoxy]-acetic acid (15 mg, 0.025 mmol) and aniline (3.4 uL, 0.037 mmol) in dichloromethane (0.2 mL) under nitrogen atmosphere was added 1-ethyl-3-(3-dimethylaminopropyl)carbodiimide (7.1 mg, 0.037 mmol) and hydroxybenzotriazole (5.6 mg, 0.037 mmol). The mixture was stirred at ambient temperature for 5 minutes. Triethylamine (10 uL, 0.074 mmol) was added to the mixture. The reaction was stirred for 12 hours. After eluting through a short pad of silica gel column, the crude material was purified by HPLC to afford the title compound (8 mg, 50% yield). MS (ESI) [m/e, (M+H)$^+$]=686.3. $^1$H NMR (400 MHz, chloroform-d) δ ppm 6.82-7.69 (m, 12H), 4.13-5.38 (m, 5H), 2.38-3.75 (m, 8H), 2.15-2.32 (m, 3H), 1.12-1.70 (m, 8H), 0.66-0.99 (m, 6H).

Example 4

[3-(3-Dibutylcarbamoyl-5-methyl-pyrazol-1-yl)-4-((S)-3-hydroxymethyl-3,4-dihydro-1H-isoquinoline-2-carbonyl)-phenoxy]-acetic acid ethyl ester

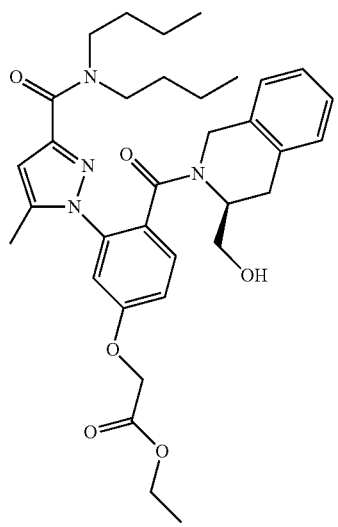 [SMILES: CCCCN(CCCC)C(=O)c1cc(C)n(-c2cc(OCC(=O)OCC)ccc2C(=O)N2Cc3ccccc3C[C@H]2CO)n1]

A solution of 1-[5-hydroxy-2-((S)-3-hydroxymethyl-3,4-dihydro-1H-isoquinoline-2-carbonyl)-phenyl]-5-methyl-1H-pyrazole-3-carboxylic acid dibutylamide (100 mg, 0.19 mmol) and potassium tert-butoxide (0.21 mL, 1 M, 0.21 mmol) in tetrahydrofuran (2 mL) was stirred at ambient temperature for 10 minutes. Ethyl 2-iodoacetate (0.027 mL, 0.23 mmol) was added and the mixture was stirred at ambient temperature for 1 hour. Ethyl acetate and aqueous HCl solution was added until the pH was about 7. The organic layer was dried over sodium sulfate and removed in vacuo. The crude material was purified by eluting through a short pad of silica gel column to afford the title compound (100 mg, 86% yield). MS (ESI) [m/e, (M+H)$^+$]=605.3. $^1$H NMR (400 MHz, chloroform-d) δ ppm 6.30-7.41 (m, 8H), 2.68-5.46 (m, 18H), 2.20-2.61 (m, 3H), 0.70-1.74 (m, 15H).

Example 5

[3-(3-Dibutylcarbamoyl-5-methyl-pyrazol-1-yl)-4-((S)-3-hydroxymethyl-3,4-dihydro-1H-isoquinoline-2-carbonyl)-phenoxy]-acetic acid

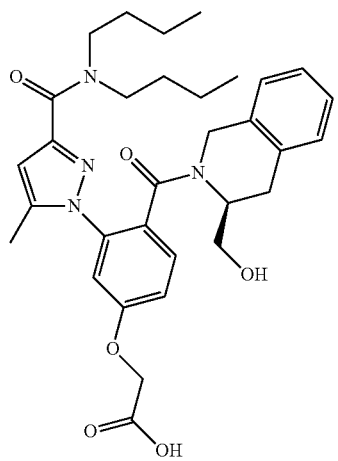 [SMILES: CCCCN(CCCC)C(=O)c1cc(C)n(-c2cc(OCC(=O)O)ccc2C(=O)N2Cc3ccccc3C[C@H]2CO)n1]

Following general method h, the title compound (60 mg, 63%) was prepared from [3-(3-dibutylcarbamoyl-5-methyl-pyrazol-1-yl)-4-((S)-3-hydroxymethyl-3,4-dihydro-1H-soquinoline-2-carbonyl)-phenoxy]-acetic acid ethyl ester. MS (ESI) [m/e, (M+H)$^+$]=577.3. $^1$H NMR (400 MHz, chloroform-d) δ ppm 6.09-7.55 (m, 8H), 3.88-5.34 (m, 5H), 2.34-3.69 (m, 8H), 2.10-2.33 (m, 3H), 0.62-1.71 (m, 14H).

Example 6

1-[2-((S)-3-Hydroxymethyl-3,4-dihydro-1H-isoquinoline-2-carbonyl)-5-phenylcarbamoylmethoxy-phenyl]-5-methyl-1H-pyrazole-3-carboxylic acid dibutylamide

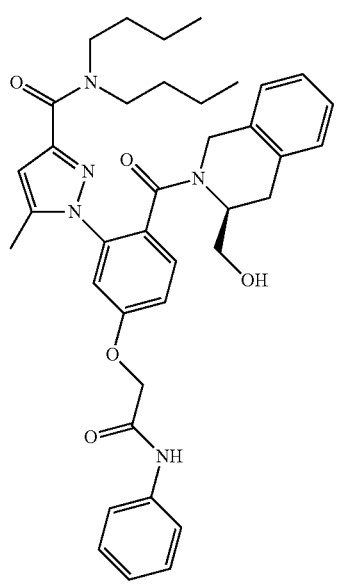 [SMILES: CCCCN(CCCC)C(=O)c1cc(C)n(-c2cc(OCC(=O)Nc3ccccc3)ccc2C(=O)N2Cc3ccccc3C[C@H]2CO)n1]

Following Preparation of 4-chloro-1-[2S)-3-hydroxymethyl-3,4-dihydro-1H-isoquinoline-2-carbonyl)-4-phenylcarbamoylmethoxy-phenyl]-5-methyl-1H-pyrazole-3-carboxylic acid dibutylamide, the title compound (5 mg, 22%) was prepared from [3-(3-dibutylcarbamoyl-5-methyl-pyrazol-1-yl)-4-((S)-3-hydroxymethyl-3,4-dihydro-1H-isoquinoline-2-carbonyl)-phenoxy]-acetic acid. MS (ESI) [m/e, (M+H)$^+$]=652.3. $^1$H NMR (400 MHz, chloroform-d) δ ppm 8.22-8.44 (m, 1H), 6.79-7.69 (m, 12H), 6.20-6.39 (m, 1H), 4.00-5.30 (m, 5H), 2.41-3.61 (m, 8H), 2.18-2.37 (m, 3H), 1.13-1.71 (m, 8H), 0.66-1.12 (m, 6H).

Example 7

[3-(3-Dibutylcarbamoyl-5-methyl-pyrazol-1-yl)-4-((S)-3-hydroxymethyl-3,4-dihydro-1H-isoquinoline-2-carbonyl)-phenoxy]-acetic acid benzyl ester

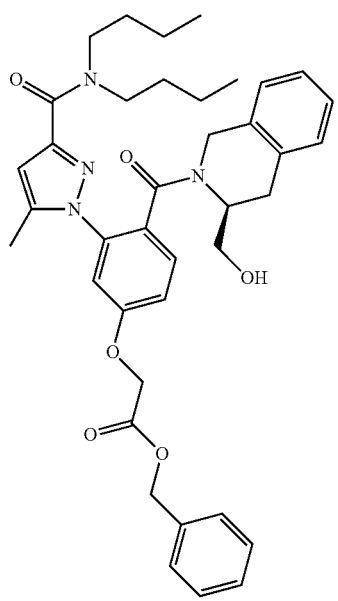 [SMILES: CCCCN(CCCC)C(=O)c1cc(C)n(-c2cc(OCC(=O)OCc3ccccc3)ccc2C(=O)N2Cc3ccccc3C[C@H]2CO)n1]

A solution of 1-[5-hydroxy-2-((S)-3-hydroxymethyl-3,4-dihydro-1H-isoquinoline-2-carbonyl)-phenyl]-5-methyl-1H-pyrazole-3-carboxylic acid dibutylamide (intermediate E, 29 mg, 0.056 mmol) and potassium tert-butoxide (0.062 mL, 1M, 0.062 mmol) in tetrahydrofuran (0.5 mL) was stirred at ambient temperature for 10 minutes. Benzyl 2-chloroacetate (0.010 mL, 0.067 mmol) was added and the mixture was stirred at ambient temperature for 2 hours. Ethyl acetate and aqueous HCl solution was added until the pH was about 7. The organic layer was eluted through a short pad of silica gel column and the crude material was purified by HPLC and prep TLC to afford the title compound (1.3 mg, 3.5% yield). MS (ESI) [m/e, (M+H)$^+$]=667.3. $^1$H NMR (400 MHz, chloroform-d) δ ppm 6.74-7.70 (m, 12H), 6.15-6.31 (m, 1H), 3.94-5.36 (m, 8H), 2.56-3.71 (m, 6H), 2.09-2.35 (m, 3H), 0.65-1.70 (m, 14H).

By repeating the procedures described in the above examples, using appropriate starting materials and HPLC method, the following compounds of Formula I, as identified in Table 1, are obtained.

TABLE 1

| Example | Structure | MW (ESI, [M + H]$^+$) | HPLC RT (min) | BCL2_SPR IC50 BAD (nM) | BCL2_SPR IC50 BAK (nM) |
|---------|-----------|------------------------|---------------|------------------------|------------------------|
| 1 | 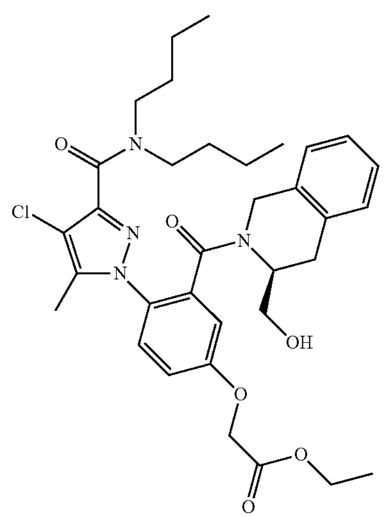 [SMILES: CCCCN(CCCC)C(=O)c1nn(-c2ccc(OCC(=O)OCC)cc2C(=O)N2Cc3ccccc3C[C@H]2CO)c(C)c1Cl] | 639.2953 | 3.77 | 509.27-514.51 | 363.16-405.06 |

TABLE 1-continued
| Example | Structure | MW (ESI, [M + H]+) | HPLC RT (min) | BCL2_SPR IC50 BAD (nM) | BCL2_SPR IC50 BAK (nM) |
|---|---|---|---|---|---|
| 2 | 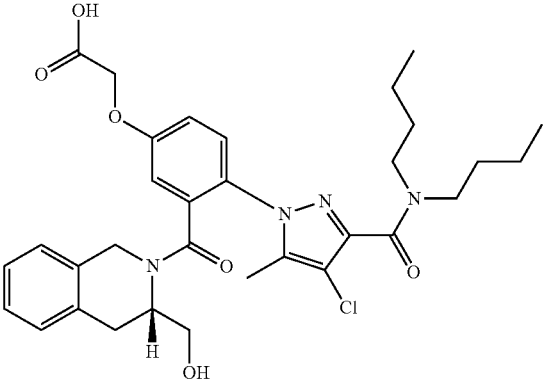 [SMILES: CCCCN(CCCC)C(=O)c1nn(-c2ccc(OCC(=O)O)cc2C(=O)N2Cc3ccccc3C[C@H]2CO)c(C)c1Cl] | 611.2644 | 2.72 | 149.12-152.68 | 132.29-137.55 |
| 3 | 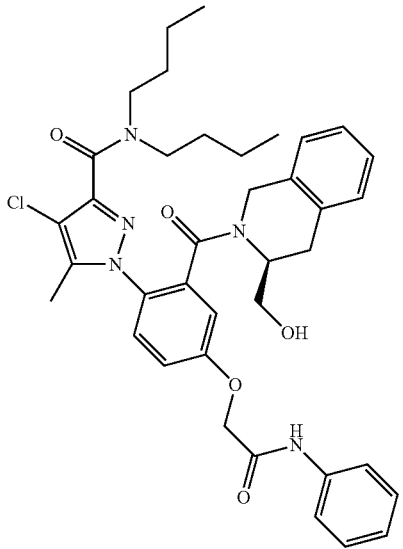 [SMILES: CCCCN(CCCC)C(=O)c1nn(-c2ccc(OCC(=O)Nc3ccccc3)cc2C(=O)N2Cc3ccccc3C[C@H]2CO)c(C)c1Cl] | 686.3101 | 3.77 | 433.2-477.33 | 406.05-436.82 |
| 4 | 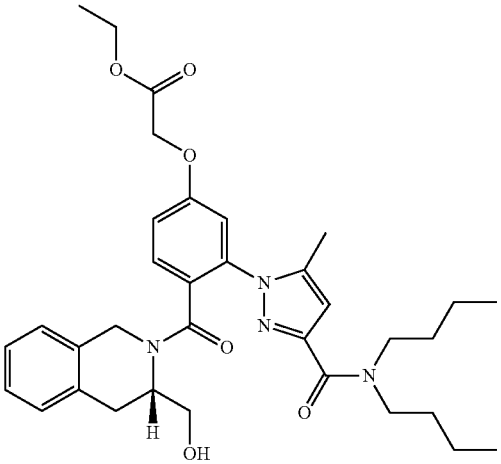 [SMILES: CCCCN(CCCC)C(=O)c1cc(C)n(-c2cc(OCC(=O)OCC)ccc2C(=O)N2Cc3ccccc3C[C@H]2CO)n1] | 605.3339 | 3.49 | 1174.5-1357.03 | 770.58-776.12 |

TABLE 1-continued

| Example | Structure | MW (ESI, [M + H]+) | HPLC RT (min) | BCL2_SPR IC50 BAD (nM) | BCL2_SPR IC50 BAK (nM) |
| --- | --- | --- | --- | --- | --- |
| 5 | 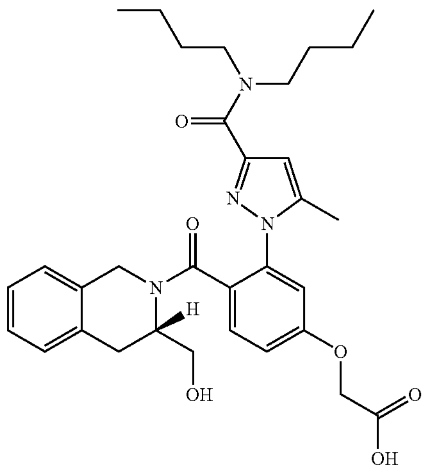 [SMILES: CCCCN(CCCC)C(=O)c1cc(C)n(-c2cc(OCC(=O)O)ccc2C(=O)N2Cc3ccccc3C[C@H]2CO)n1] | 577.3017 | 2.50 | 98.89-105.15 | 82.26-87.35 |
| 6 | 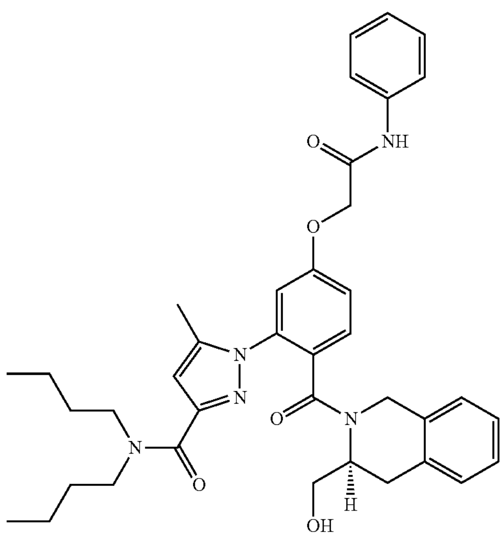 [SMILES: CCCCN(CCCC)C(=O)c1cc(C)n(-c2cc(OCC(=O)Nc3ccccc3)ccc2C(=O)N2Cc3ccccc3C[C@H]2CO)n1] | 652.3493 | 3.51 | 2085.97-2099.47 | 1269.8-1303.94 |
| 7 | 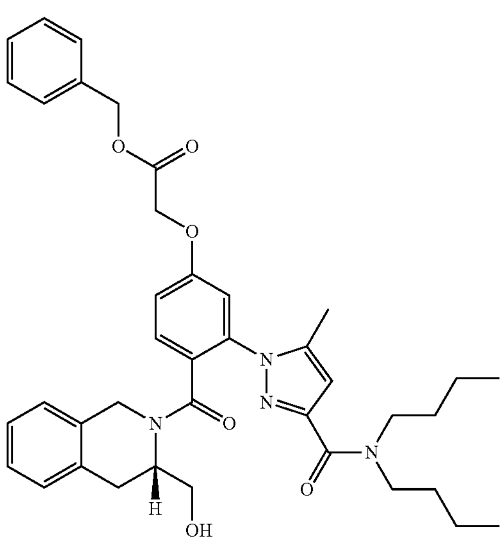 [SMILES: CCCCN(CCCC)C(=O)c1cc(C)n(-c2cc(OCC(=O)OCc3ccccc3)ccc2C(=O)N2Cc3ccccc3C[C@H]2CO)n1] | 667.3499 | 3.80 | 1520.26-1558.28 | 1250-1315.54 |

TABLE 1-continued
| Example | Structure | MW (ESI, [M + H]+) | HPLC RT (min) | BCL2_SPR IC50 BAD (nM) | BCL2_SPR IC50 BAK (nM) |
|---|---|---|---|---|---|
| 8 | 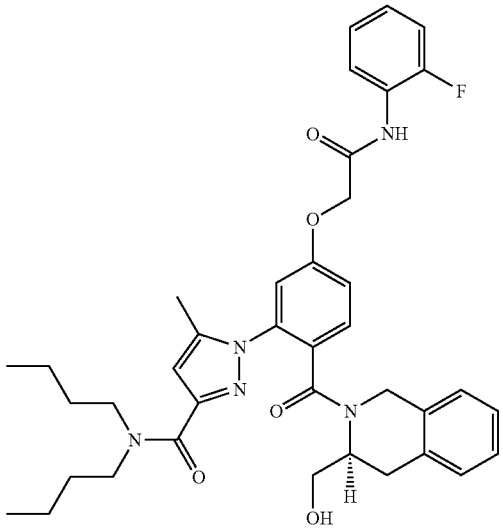 [SMILES: CCCCN(CCCC)C(=O)c1cc(C)n(-c2cc(OCC(=O)Nc3ccccc3F)ccc2C(=O)N2Cc3ccccc3C[C@H]2CO)n1] | 670.3406 | 3.53 | 2884.1-3002.68 | 1697.31-1735.6 |
| 9 | 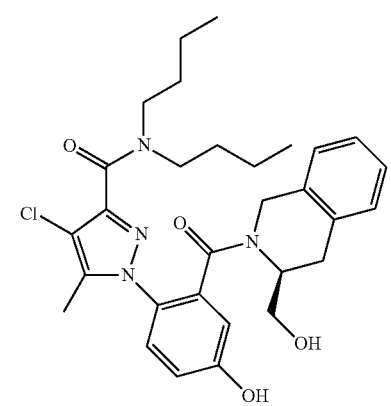 [SMILES: CCCCN(CCCC)C(=O)c1nn(-c2ccc(O)cc2C(=O)N2Cc3ccccc3C[C@H]2CO)c(C)c1Cl] | 553.2605 | 3.41 | 618.16-628.96 | 402.78-440.97 |
| 10 | 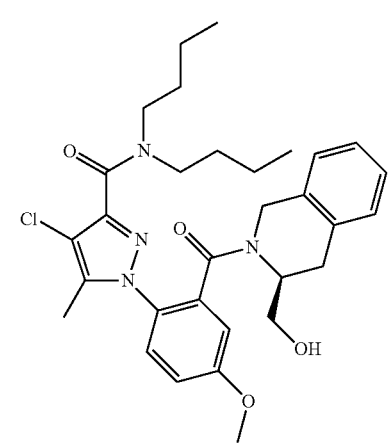 [SMILES: CCCCN(CCCC)C(=O)c1nn(-c2ccc(OC)cc2C(=O)N2Cc3ccccc3C[C@H]2CO)c(C)c1Cl] | 567.2752 | 6.30 | 1368.33-1689.85 | 815.31-969.46 |

TABLE 1-continued

| Example | Structure | MW (ESI, [M + H]+) | HPLC RT (min) | BCL2_SPR IC50 BAD (nM) | BCL2_SPR IC50 BAK (nM) |
|---|---|---|---|---|---|
| 11 | 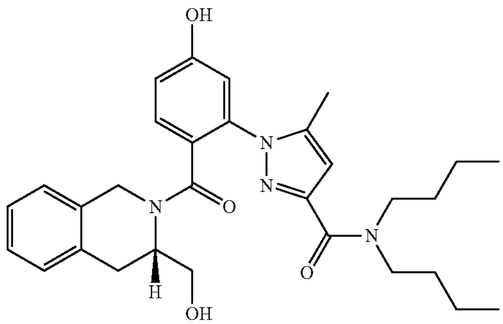 [SMILES: CCCCN(CCCC)C(=O)c1cc(C)n(-c2cc(O)ccc2C(=O)N2Cc3ccccc3C[C@H]2CO)n1] | 519.2957 | 3.08 | 258.17-298.64 | 238.27-255.62 |
| 12 | 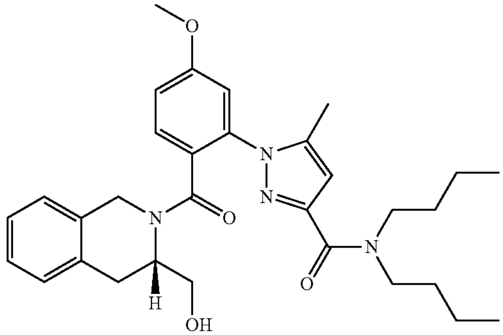 [SMILES: CCCCN(CCCC)C(=O)c1cc(C)n(-c2cc(OC)ccc2C(=O)N2Cc3ccccc3C[C@H]2CO)n1] | 533.3129 | 3.41 | 446.85-493.23 | 266.69-298.94 |

BCL-2 binding can be determined using a variety of known methods. One such assay is a sensitive and quantitative in vitro binding assay using fluorescence polarization (FP) described by Wang, J.-L.; Zhang, Z-J.; Choksi, S.; Sjam. S.; Lu, Z.; Croce, C. M.; Alnemri, E. S.; Komgold, R.; Huang, Z. Cell permeable BCL-2 binding peptides: a chemical approach to apoptosis induction in tumor cells. Cancer Res. 2000, 60, 1498-1502).

Methods for Determining IC50s

The present method includes utility of a Surface plasmon resonance (SPR)-based biosensor (Biacore™' GE Healthcare, Uppsala, Sweden) to characterize BCL-2 inhibitors.

Biacore™ utilizes the phenomenon of surface plasmon resonance (SPR) to detect and measure binding interactions. In a typical Biacore experiment, one of the interacting molecules (ligand) is immobilized on a flexible dextran matrix while the interacting partner (analyte) is allowed to flow across that surface. A binding interaction results in an increase in mass on the sensor surface and a corresponding direct change in the refractive index of the medium in the vicinity of the sensor surface. Changes in refractive index or signal are recorded in resonance units (R.U.) Signal changes due to association and dissociation of complexes are monitored in a non-invasive manner, continuously and in real-time, the results of which are reported in the form of a sensorgram.

The SPR assay is configured to examine solution inhibition of BCL-2 binding to peptide derivatized sensor surfaces to generate IC50 values as a measure of inhibitor potency.

Solution Inhibition Assay Format:

Biacore™ A100 (GE Healthcare, Uppsala, Sweden) was used to conduct all experiments reported herein. Sensor surface preparation and all interaction analyses experiments were performed at 25° C. Reagents were purchased from GE Healthcare. Running buffer containing 10 mM Hepes, pH7.4, 150 mM sodium chloride, 1.25 mM Dithiothreitol, 3% Dimethyl sulfoxide and 0.05% polysorbate 20 were utilized throughout all analyses.

Biotinylated BAK, BAD and NOXA peptides were diluted to 10 nM in running buffer and captured onto a sensor surface pre-derivatized with streptavidin (sensor chip SA) to peptide surface densities in the range 50-100 R.U. Peptide captured surfaces were blocked with 50004 PEO$_2$-Biotin. A blank detection spot in each flowcell was similarly blocked with PEO$_2$-biotin and served as a reference spot in the competition assay.

Interaction analyses were performed by first equilibrating each sample within a 6 point three fold compound dilution series in the range 1604 to 0.004 nM with 56 nM BCL-2 for one hour during instrument start-up procedures. Protein compound mixtures were then injected over each peptide surface in parallel for 60 seconds at a flow-rate of 30 μL/min. 56 nM BCL-2 control samples were also prepared and run at regular intervals during the assay. Surface regeneration was performed at the end of each analysis cycle by two 30 second injections of 10 mM Glycine, pH 2.5, 1M Sodium Chloride, 0.05% polysorbate 20. Samples and control compound samples were run in duplicate and controls are also run at regular intervals during the assay to monitor surface and assay performance.

Data analyses are carried out using Biacore™ A100 evaluation software v1.1 to validate assay quality. Binding level report points were used relative to BCL-2 control samples to calculate % inhibition values for each compound protein mixture. These data are then plotted versus compound concentration and analyzed in Tibco® Spotfire® v2.1 via logistic regression to calculate IC$_{50}$ values for each compound. The range of data shown in table 1 represents the high and low IC$_{50}$ values obtained from multiple experiments.

Caspase Activation Assay Method

In cancer cell lines that depend on BCL2 for survival, such as the Caki-2 kidney clear cell carcinoma cell line, inhibition of BCL2 induces apoptosis characterized by activation of caspases. Compounds of the invention are tested for ability to induce caspase activation in the Caki-2 cell line as follows. On day one, 2500 Caki-2 cells are plated into 384 well tissue culture plates. On day two, cells are treated with a dose range of a compound of the invention in Opti-MEM media (Invtrogen) containing 1% fetal bovine serum for four hours. At four hours post-treatment relative levels of caspase activation, relative to baseline levels in vehicle treated cells, are assessed using the Caspase-glo reagent from Promega.

Cell Proliferation Assay Method

Compounds of the invention are tested for their ability to impact cell proliferation and/or survival in the Caki-2 cell line as follows. On day one, 2500 Caki-2 cells are plated into 384 well tissue culture plates. On day two, cells are treated with a dose range of a compound of the invention in Opti-MEM media (Invitrogen) containing 1% fetal bovine serum for 24 hours. At 24 hours post-treatment, cell viability, relative to vehicle treated cells, is assessed using the ATPLite reagent from Perkin Elmer.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

The invention claimed is:

1. A compound of formula:

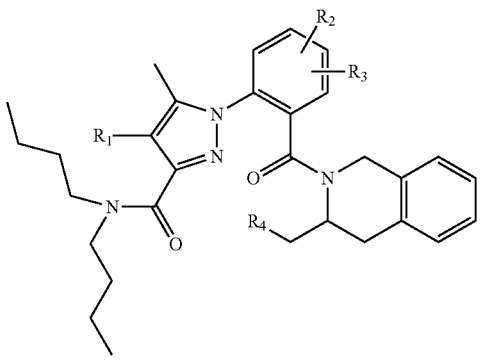

in which:

$R_1$ is selected from hydrogen and halo;

$R_2$ is selected from hydrogen and $C_{1-4}$alkyl; wherein $R_2$ is in the meta position and $R_3$ is in the para position relative to the pyrazole ring or $R_2$ is in the para position and $R_3$ is in the meta position relative to the pyrazole ring;

$R_3$ is selected from hydroxy and L-$R_5$; wherein L is selected from —$OX_1C(O)$—, —$OX_1C(O)O$—, —$OX_1$— and —$OX_1C(O)NH$—; wherein $X_1$ is selected from a bond and branched or unbranched $C_{1-4}$alkylene; wherein said alkylene of $X_1$ can be unsubstituted or substituted with a group selected from carboxy-methyl, methoxy-carbonyl-methyl, methyl-carbonyl-amino and phenyl;

$R_4$ is selected from hydrogen, hydroxy, —$X_3NR_8R_9$, —$X_3C(O)OR_8$, —$X_3OR_8$, —$X_3C(O)NR_8R_9$ and —$X_3NR_8C(O)R_9$; wherein $X_3$ is selected from a bond and $C_{1-4}$alkylene; and $R_8$ and $R_9$ are independently selected from hydrogen, $C_{1-4}$alkyl and phenyl; or $R_8$ and $R_9$ together with the nitrogen to which $R_8$ and $R_9$ are attached form a 5 to 7 member saturated ring containing 1 to 3 groups or heteroatoms independently selected from $C(O)$, $NR_{10}$, O and $S(O)_{0-2}$; wherein $R_{10}$ is selected from hydrogen and $C_{1-4}$alkyl;

$R_5$ is selected from hydrogen, $C_{1-6}$alkyl, $C_{2-6}$alkenyl, cyclopropyl, imidazo[1,2-a]pyrimidinyl, 2-oxo-4-phenylpiperazin-1-yl, 4-(2-chlorobenzyl)-3-oxopiperazin-1-yl, imidazo[1,2-a]pyridinyl, benzo[d]isoxazolyl, naphtho[2,1-d][1,2,3]oxadiazol-5-yl, 1H-pyrrolo[2,3-b]pyridinyl, imidazo[2,1-b]thiazolyl, 1H-pyrazolo[3,4-b]pyridinyl, benzo[c][1,2,5]thiadiazolyl, 4-oxo-4,5,6,7-tetrahydrobenzofuranyl, 2-oxo-1,2,3,6-tetrahydropyrimidinyl, 1,2,4-oxadiazolyl, 2,3-dihydrobenzo[b][1,4]dioxin-2-yl, naphtho[2,3-d][1,3]dioxol-2-yl, 3,4-dihydro-2H-benzo[b][1,4]oxazin-7-yl, 2,3-dihydrobenzofuran-3-yl, chroman-8-yl, 3-oxo-3H-pyrazolyl, 6-oxo-1,6-dihydropyridazinyl, benzo[b]thiophenyl, benzo[b]furanyl, 2-oxo-1,2-dihydropyridinyl, 2-oxo-1,2,5,6,7,8-hexahydroquinolinyl, 4-oxo-1,4-dihydro-1,8-naphthyridinyl, 4-oxo-4H-pyrano[2,3-b]pyridinyl, 10,10-dioxido-9-oxo-9H-thioxanthen-3-yl, 5-oxopyrrolidin-3-yl, phenyl, quinolinyl, isoquinolinyl, phenoxy, phenylthio, benzoxy, phenoxy-methyl, phenyl-sulfonyl, furanyl, thiazolyl, oxazolyl, isoxazolyl, thienyl, pyrrolyl, quinolin-8-yloxy, pyrimidinyl, pyridinyl, pyrrolidinyl, pyrrolidinonyl, imidazolidine-2,4-dionyl, piperidinyl, piperazinyl, pyrazinyl, pyrazolyl, morpholino, oxomorpholino, indolyl, benzo[d][1,2,3]triazol and oxopiperazinyl; wherein said $C_{1-6}$alkyl, $C_{2-6}$alkenyl, cyclopropyl, imidazo[1,2-a]pyrimidinyl, benzo[d]isoxazolyl, imidazo[1,2-a]pyridinyl, 4-oxo-4,5,6,7-tetrahydrobenzofuranyl, 2-oxo-1,2,3,6-tetrahydropyrimidinyl, imidazo[2,1-b]thiazolyl, 1H-pyrrolo[2,3-b]pyridinyl, 1H-pyrazolo[3,4-b]pyridinyl, 1,2,4-oxadiazolyl, benzo[c][1,2,5]thiadiazolyl, 2,3-dihydrobenzo[b][1,4]dioxin-2-yl, naphtho[2,3-d][1,3]dioxol-2-yl, 3,4-dihydro-2H-benzo[b][1,4]oxazin-7-yl, 2,3-dihydrobenzofuran-3-yl, chroman-8-yl, 3-oxo-3H-pyrazolyl, 6-oxo-1,6-dihydropyridazinyl, 2-oxo-1,2-dihydropyridinyl, 2-oxo-1,2,5,6,7,8-hexahydroquinolinyl, 4-oxo-1,4-dihydro-1,8-naphthyridinyl, 4-oxo-4H-pyrano[2,3-b]pyridinyl, 10,10-dioxido-9-oxo-9H-thioxanthen-3-yl, 5-oxopyrrolidin-3-yl, phenyl, quinolinyl, isoquinolinyl, phenoxy, benzoxy, phenoxymethyl, phenylthio, phenyl-sulfonyl, furanyl, thiazolyl, oxazolyl, isoxazolyl, thienyl, pyridinyl, pyrrolyl, quinolin-8-yloxy, pyrrolidinyl, pyrimidinyl, pyrrolidinonyl, piperazinyl, piperidinyl, pyrazinyl, pyrazolyl, morpholino, oxomorpholino, indolyl, benzo[d][1,2,3]triazol or oxopiperazinyl of $R_5$ is unsubstituted or substituted with 1 to 3 groups independently selected from halo, cyano, nitro, —$NR_6R_7$, $C_{1-4}$alkyl, halo-substituted-$C_{1-4}$alkyl, $C_{1-4}$alkoxy, halo-substituted-$C_{1-4}$alkoxy, halo-substituted-$C_{1-4}$alkylthio, —$C(O)OR_6$, —$X_3OR_6$, —$C(O)R_6$, —$C(O)NR_6R_7$, —$NR_6S(O)_2X_{37}$, —$X_3NR_6C(O)R_7$, —$S(O)_{0-2}R_6$, —$S(O)_{0-2}NR_6R_7$, phenyl, pyridinyl, benzyl, piperidinyl, pyrrolidinyl, morpholino, morpholino-methyl, 1,3-dioxoisoindolinyl, 1,2,4-oxadiazolyl, pyrazolyl, phenoxy, indolyl, (1H-1,2,4-triazolyl)methyl and benzoxy; wherein $R_6$ and $R_7$ are independently selected from hydrogen, $C_{1-4}$alkyl, $C_{3-8}$cycloalkyl, pyridinyl, phenyl, benzyl and naphthyl; wherein said phenyl, pyridinyl, benzyl, morpholino, morpholino-methyl, 1,3-dioxoisoindolinyl, 1,2,4-oxadiazolyl, pyrazolyl, indolyl and benzoxy substituents of $R_5$ or said pyridinyl and phenyl of $R_6$ can be unsubstituted or further substituted with a group selected from halo, nitro, amino-sulfonyl, $C_{1-4}$alkyl, $C_{1-4}$alkoxy and halo-substituted-$C_{1-4}$alkyl; wherein $X_3$ is selected from a bond and $C_{1-4}$alkylene; or the pharmaceutically acceptable salt thereof; with the proviso that compounds of formula I do not include the two compounds where $R_1$ is hydrogen, $R_2$ is hydrogen and $R_3$ is a group selected from —OCH$_2$C(O)-phenyl and —OCH$_2$C(O)OH, or a pharmaceutically acceptable salt thereof.

2. The compound of claim 1 of formula:

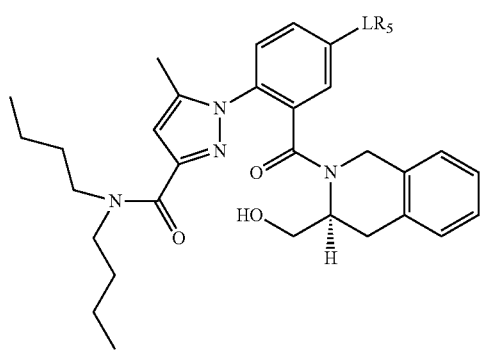

in which:

L is selected from —OCH$_2$C(O)—, —OCH$_2$C(O)O—, —O— and —OCH$_2$C(O)NH—; and $R_5$ is selected from hydrogen, methyl, ethyl, phenyl and benzyl; wherein said phenyl or benzyl are unsubstituted or substituted with halo, or a pharmaceutically acceptable salt thereof.

3. The compound of claim 1 selected from:

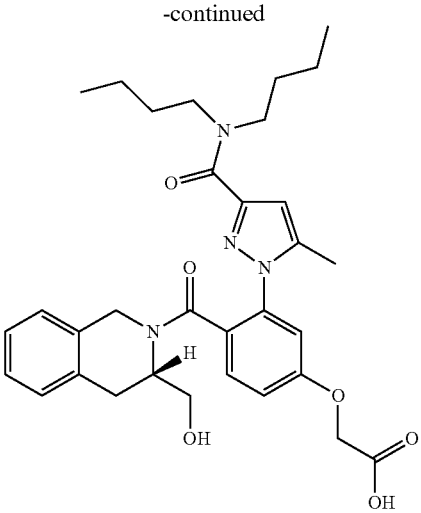

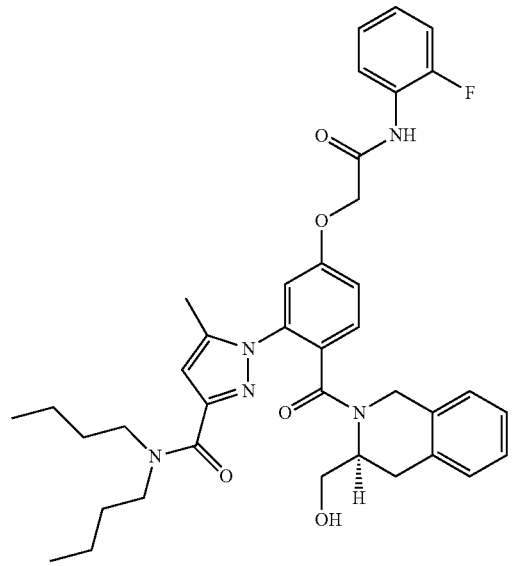

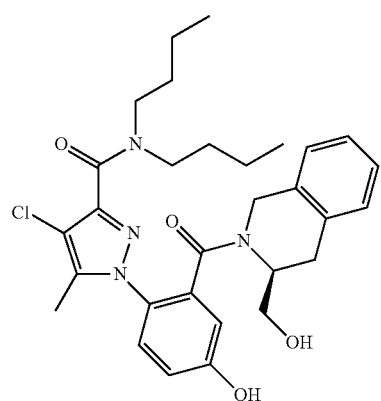

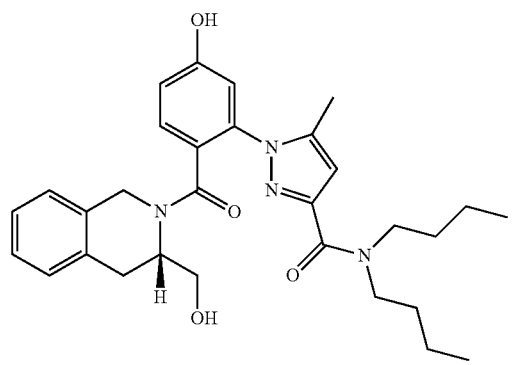

67
-continued
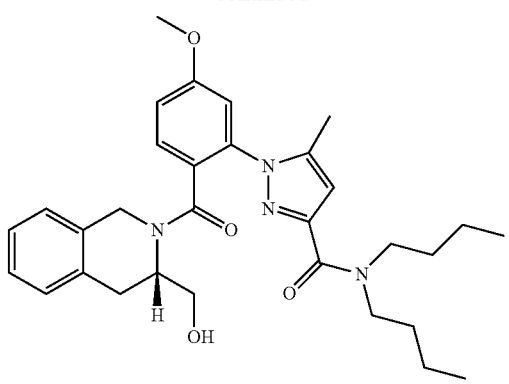
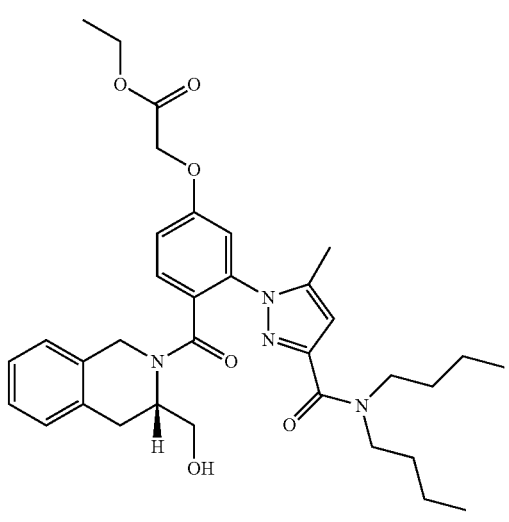
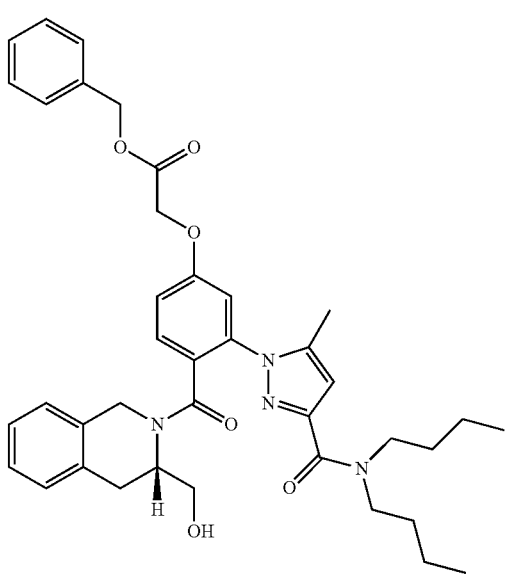
68
-continued
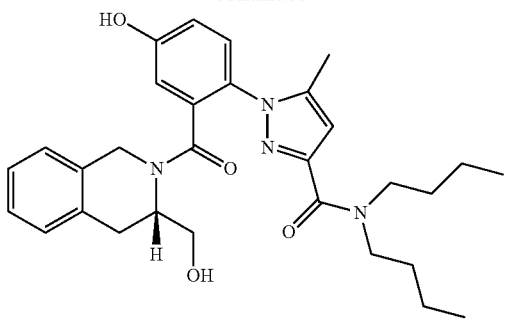
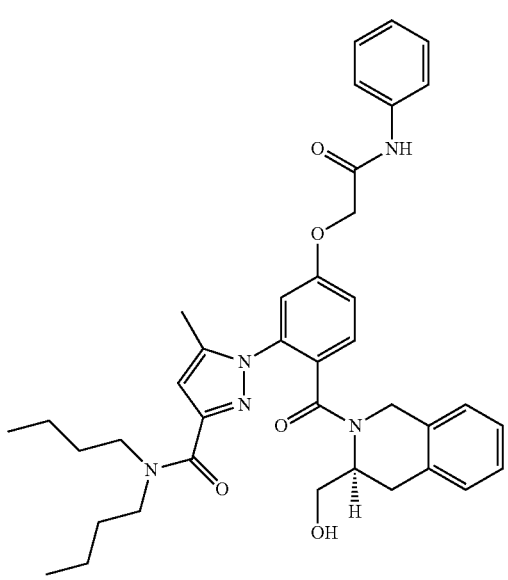
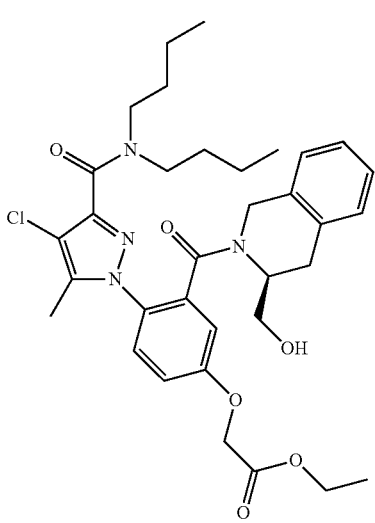

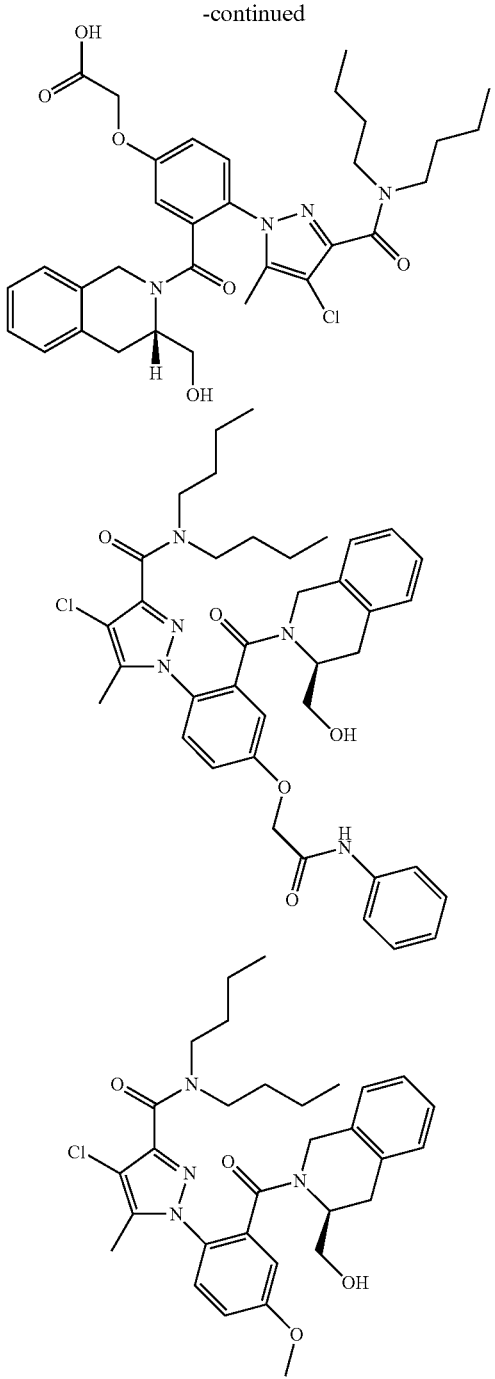

or a pharmaceutically acceptable salt thereof.

4. A compound of claim 1 or salt thereof in combination with one or more therapeutically active agents.

5. The compound of claim 1, or a pharmaceutically acceptable salt thereof, wherein:
L is selected from —$OX_1$— and —$OX_1C(O)NH$—; and
$R_5$ is selected from hydrogen, $C_{1-6}$alkyl, $C_{2-6}$alkenyl, cyclopropyl, imidazo[1,2-a]pyrimidinyl, 2-oxo-4-phenylpiperazin-1-yl, 4-(2-chlorobenzyl)-3-oxopiperazin-1-yl, imidazo[1,2-a]pyridinyl, benzo[d]isoxazolyl, naphtho[2,1-d][1,2,3]oxadiazol-5-yl, 1H-pyrrolo[2,3-b]pyridinyl, imidazo[2,1-b]thiazolyl, 1H-pyrazolo[3,4-b]pyridinyl, benzo[c][1,2,5]thiadiazolyl, 4-oxo-4,5,6,7-tetrahydrobenzofuranyl, 2-oxo-1,2,3,6-tetrahydropyrimidinyl, 1,2,4-oxadiazolyl, 2,3-dihydrobenzo[b][1,4]dioxin-2-yl, naphtho[2,3-d][1,3]dioxol-2-yl, 3,4-dihydro-2H-benzo[b][1,4]oxazin-7-yl, 2,3-dihydrobenzofuran-3-yl, chroman-8-yl, 3-oxo-3H-pyrazolyl, 6-oxo-1,6-dihydropyridazinyl, benzo[b]thiophenyl, benzo[b]furanyl, 2-oxo-1,2-dihydropyridinyl, 2-oxo-1,2,5,6,7,8-hexahydroquinolinyl, 4-oxo-1,4-dihydro-1,8-naphthyridinyl, 4-oxo-4H-pyrano[2,3-b]pyridinyl, 10,10-dioxido-9-oxo-9H-thioxanthen-3-yl, 5-oxopyrrolidin-3-yl, phenyl, quinolinyl, isoquinolinyl, phenoxy, phenylthio, benzoxy, phenoxy-methyl, phenyl-sulfonyl, furanyl, thiazolyl, oxazolyl, isoxazolyl, thienyl, pyrrolyl, quinolin-8-yloxy, pyrimidinyl, pyridinyl, pyrrolidinyl, pyrrolidinonyl, imidazolidine-2,4-dionyl, piperidinyl, piperazinyl, pyrazinyl, pyrazolyl, morpholino, oxomorpholino, indolyl, benzo[d][1,2,3]triazol and oxopiperazinyl; wherein said $C_{1-6}$ alkyl, $C_{2-6}$alkenyl, cyclopropyl, imidazo[1,2-a]pyrimidinyl, benzo[d]isoxazolyl, imidazo[1,2-a]pyridinyl, 4-oxo-4,5,6,7-tetrahydrobenzofuranyl, 2-oxo-1,2,3,6-tetrahydropyrimidinyl, imidazo[2,1-b]thiazolyl, 1H-pyrrolo[2,3-b]pyridinyl, 1H-pyrazolo[3,4-b]pyridinyl, 1,2,4-oxadiazolyl, benzo[c][1,2,5]thiadiazolyl, 2,3-dihydrobenzo[b][1,4]dioxin-2-yl, naphtho[2,3-d][1,3]dioxol-2-yl, 3,4-dihydro-2H-benzo[b][1,4]oxazin-7-yl, 2,3-dihydrobenzofuran-3-yl, chroman-8-yl, 3-oxo-3H-pyrazolyl, 6-oxo-1,6-dihydropyridazinyl, 2-oxo-1,2-dihydropyridinyl, 2-oxo-1,2,5,6,7,8-hexahydroquinolinyl, 4-oxo-1,4-dihydro-1,8-naphthyridinyl, 4-oxo-4H-pyrano[2,3-b]pyridinyl, 10,10-dioxido-9-oxo-9H-thioxanthen-3-yl, 5-oxopyrrolidin-3-yl, phenyl, quinolinyl, isoquinolinyl, phenoxy, benzoxy, phenoxymethyl, phenylthio, phenyl-sulfonyl, furanyl, thiazolyl, oxazolyl, isoxazolyl, thienyl, pyridinyl, pyrrolyl, quinolin-8-yloxy, pyrrolidinyl, pyrimidinyl, pyrrolidinonyl, piperazinyl, piperidinyl, pyrazinyl, pyrazolyl, morpholino, oxomorpholino, indolyl, benzo[d][1,2,3]triazol or oxopiperazinyl of $R_5$ is unsubstituted or substituted with 1 to 3 groups independently selected from halo, cyano, nitro, —$NR_6R_7$, $C_{1-4}$alkyl, halo-substituted-$C_{1-4}$ alkyl, $C_{1-4}$alkoxy, halo-substituted-$C_{1-4}$ alkoxy, halo-substituted-$C_{1-4}$alkylthio, —$X_3OR_6$, —$C(O)R_6$, —$C(O)NR_6R_7$, —$NR_6S(O)_2X_3R_7$, —$X_3NR_6C(O)R_7$, —$S(O)_{0-2}R_6$, —$S(O)_{0-2}NR_6R_7$, phenyl, pyridinyl, benzyl, piperidinyl, pyrrolidinyl, morpholino, morpholino-methyl, 1,3-dioxoisoindolinyl, 1,2,4-oxadiazolyl, pyrazolyl, phenoxy, indolyl, (1H-1,2,4-triazolyl)methyl and benzoxy; wherein $R_6$ and $R_7$ are independently selected from hydrogen, $C_{1-4}$alkyl, $C_{3-8}$cycloalkyl, pyridinyl, phenyl, benzyl and naphthyl; wherein said phenyl, pyridinyl, benzyl, morpholino, morpholino-methyl, 1,3-dioxoisoindolinyl, 1,2,4-oxadiazolyl, pyrazolyl, indolyl and benzoxy substituents of $R_5$ or said pyridinyl and phenyl of $R_6$ can be unsubstituted or further substituted with a group selected from halo, nitro, amino-sulfonyl, $C_{1-4}$alkyl, $C_{1-4}$alkoxy and halo-substituted-$C_{1-4}$alkyl; wherein $X_3$ is selected from a bond and $C_{1-4}$alkylene.

6. The compound of claim 1, or a pharmaceutically acceptable salt thereof, wherein $R_1$ is hydrogen or chloro.

7. The compound of claim 1, or a pharmaceutically acceptable salt thereof, wherein $R_2$ is hydrogen.

8. The compound of claim 1, or a pharmaceutically acceptable salt thereof, wherein $R_4$ is hydroxy.

9. The compound of claim 1, or a pharmaceutically acceptable salt thereof, wherein
$R_1$ is hydrogen or chloro;
$R_2$ is hydrogen; and
$R_4$ is hydroxy.

10. The compound of claim 1, or a pharmaceutically acceptable salt thereof, wherein the group

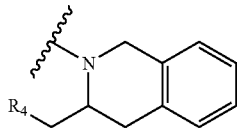

has the (S) stereochemistry.

11. The compound of claim 1, or a pharmaceutically acceptable salt thereof, wherein:
$R_3$ is hydroxy or -L-$R_5$; wherein L is selected from —$OX_1C(O)$—, —$OX_1C(O)O$—, —$OX_1$— and —$OX_1C(O)NH$—; wherein $X_1$ is unbranched $C_{1-4}$alkylene; and
$R_5$ is selected from hydrogen, $C_{1-6}$alkyl, or phenyl, wherein the phenyl is unsubstituted or substituted with halo.

12. The compound of claim 11, or a pharmaceutically acceptable salt thereof, wherein:
L is selected from —$OX_1C(O)O$— and —$OX_1C(O)NH$—.

13. The compound of claim 12, or a pharmaceutically acceptable salt thereof, wherein
$R_1$ is hydrogen or chloro;
$R_2$ is hydrogen; and
$R_4$ is hydroxy.

14. The compound of claim 11, or a pharmaceutically acceptable salt thereof, wherein
$R_1$ is hydrogen or chloro;
$R_2$ is hydrogen; and
$R_4$ is hydroxy.

15. The compound of claim 14, or a pharmaceutically acceptable salt thereof, wherein the group

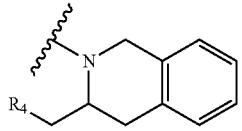

has the (S) stereochemistry.

16. A pharmaceutical composition comprising a compound of claim 1 or a pharmaceutically acceptable salt thereof, and at least one pharmaceutically acceptable carrier.

17. A method of treating cancer comprising administering a compound of claim 1, or a pharmaceutically acceptable salt thereof, to a person in need of such treatment in an effective amount for the prophylactic or therapeutic treatment of cancer wherein the cancer is selected from prostate, hormone resistant prostate, breast, non-small cell lung, small cell lung, colorectal, melanoma, head, neck and pancreatic cancer.

* * * * *